United States Patent
Gray, Jr. et al.

(10) Patent No.: US 12,398,236 B2
(45) Date of Patent: Aug. 26, 2025

(54) ABSORBABLE COPOLYMERS WITH IMPROVED THERMAL STABILITY

(71) Applicant: Poly-Med, Inc., Anderson, SC (US)

(72) Inventors: Kenneth David Gray, Jr., Columbia, SC (US); Michael Aaron Vaughn, Anderson, SC (US)

(73) Assignee: Poly-Med, Inc., Anderson, SC (US)

( * ) Notice: Subject to any disclaimer, the term of this patent is extended or adjusted under 35 U.S.C. 154(b) by 0 days.

(21) Appl. No.: 16/536,093

(22) Filed: Aug. 8, 2019

(65) Prior Publication Data

US 2019/0359768 A1 Nov. 28, 2019

Related U.S. Application Data

(63) Continuation of application No. 14/975,303, filed on Dec. 18, 2015, now abandoned.

(60) Provisional application No. 62/094,723, filed on Dec. 19, 2014.

(51) Int. Cl.

| | | |
|---|---|---|
| *C08G 63/64* | (2006.01) | |
| *A61L 15/26* | (2006.01) | |
| *A61L 15/64* | (2006.01) | |
| *A61L 27/34* | (2006.01) | |
| *A61L 27/54* | (2006.01) | |
| *A61L 27/58* | (2006.01) | |
| *A61L 31/10* | (2006.01) | |
| *A61L 31/14* | (2006.01) | |
| *A61L 31/16* | (2006.01) | |
| *C08G 63/85* | (2006.01) | |
| *C08G 63/91* | (2006.01) | |

(52) U.S. Cl.
CPC .............. *C08G 63/64* (2013.01); *A61L 15/26* (2013.01); *A61L 15/64* (2013.01); *A61L 27/34* (2013.01); *A61L 27/54* (2013.01); *A61L 27/58* (2013.01); *A61L 31/10* (2013.01); *A61L 31/148* (2013.01); *A61L 31/16* (2013.01); *C08G 63/85* (2013.01); *C08G 63/91* (2013.01); *A61L 2300/604* (2013.01); *A61L 2300/606* (2013.01)

(58) Field of Classification Search
CPC .... C08G 63/64; A61L 31/10; C08J 2300/206; C08J 2400/206; C10N 2220/029
See application file for complete search history.

(56) References Cited

U.S. PATENT DOCUMENTS

| | | | |
|---|---|---|---|
| 5,462,169 | A | 10/1995 | Dygert |
| 5,639,831 | A | 6/1997 | Himes et al. |
| 6,342,065 | B1 | 1/2002 | Shalaby |
| 6,462,169 | B1 | 10/2002 | Shalaby |
| 6,498,229 | B1 | 12/2002 | Shalaby |
| 7,265,186 | B2 | 9/2007 | Zhao |
| 8,128,954 | B2 | 3/2012 | Davis et al. |
| 8,262,723 | B2 | 9/2012 | Wang et al. |
| 8,569,421 | B2 | 10/2013 | Jakubowski et al. |
| 2005/0149158 | A1 | 7/2005 | Hunter et al. |
| 2006/0240063 | A9 | 10/2006 | Hunter et al. |
| 2008/0119848 | A1 | 5/2008 | Shalaby et al. |
| 2013/0272997 | A1* | 10/2013 | Gray, Jr. ............. A61L 24/0015 424/78.38 |

FOREIGN PATENT DOCUMENTS

| | | |
|---|---|---|
| EP | 15871232.3 | 7/2017 |
| JP | H09188806 A | 7/1997 |
| JP | 2004131692 A | 4/2004 |
| JP | H0912689 A | 8/2004 |
| JP | 2003515640 A | 10/2011 |
| JP | 2010508923 A | 7/2013 |
| JP | 2017-533270 | 7/2017 |
| WO | PCT/US2015/066869 | 12/2015 |

OTHER PUBLICATIONS

Stjerndahl et al. "Minimization of residual tin in the controlled Sn(II)octoate-catalyzed polymerization of e-caprolactone", Journal of Biomedical Materials Research Part A, Dec. 2008 pp. 843-1122 (Year: 2008).*
U.S. Appl. No. 62/094,723, filed Dec. 19, 2014, Gray, K., et al.
U.S. Appl. No. 14/975,303, filed Dec. 18, 2015, Shalaby, S.W.
Inernational Search Report, and Written Opinion, Issued Feb. 25, 2016, for International Patent Application PCT/US015/066869, 9 p.
International Preliminary Report on Patentability, issued Jun. 20, 2017, for International Patent Application PCT/US015/066869, 7 p.
Office Action, issued Apr. 8, 2020, in EP 15871232.3, filed Jul. 14, 2017, 4 p.
European Search Report, issued Jul. 16, 2018, 5 p.
Office Action, issued Sep. 20, 2019, in JP 2017-533270, 3 p.
Decision to Grant, issued Jul. 28, 2020, in JP 2017-533270, 6 p.
Notice of Abandonment, issued Dec. 12, 2019, in U.S. Appl. No. 14/975,3030, filed Dec. 18, 2015, 2 p.
Final Office Action, issued Apr. 8, 2019, in U.S. Appl. No. 14/975,3030, filed Dec. 18, 2015, 8 p.
Response to NonFinal Office Action, issued Jan. 1, 2019, in U.S. Appl. No. 14/975,3030, filed Dec. 18, 2015, 10 p.
NonFinal Office Action, issued Nov. 1, 2018, in U.S. Appl. No. 14/975,3030, filed Dec. 18, 2015, 8 p.
Response to Final Office Action, issued Jul. 26, 2018, in U.S. Appl. No. 14/975,3030, filed Dec. 18, 2015, 10 p.
Final Office Action, issued Apr. 26, 2028, in U.S. Appl. No. 14/975,3030, filed Dec. 18, 2015, 9 p.
Response to NonFinal Office Action, issued Feb. 25, 2018, in U.S. Appl. No. 14/975,3030, filed Dec. 18, 2015, 11 p.

(Continued)

*Primary Examiner* — James W Rogers
(74) *Attorney, Agent, or Firm* — Meunier Carlin & Curfman LLC

(57) ABSTRACT

The present invention relates to absorbable block copolymers with improved characteristics including thermal stability, molecular weight consistency, inherent viscosity retention following melt extrusion, and fibers made from the polymers exhibit increased strength.

11 Claims, 13 Drawing Sheets

(56) References Cited

OTHER PUBLICATIONS

NonFinal Office Action, issued Oct. 25, 2017, in U.S. Appl. No. 14/975,3030, filed Dec. 18, 2015, 9 p.
Response to Restriction Requirement, issued Sep. 29, 2017, in U.S. Appl. No. 14/975,3030, filed Dec. 18, 2015, 6 p.
Restriction Requirement, issued Jun. 29, 2017, in U.S. Appl. No. 14/975,3030, filed Dec. 18, 2015, 7 p.
Response to Notice to Correct, issued Mar. 4, 2016, in U.S. Appl. No. 14/975,3030, filed Dec. 18, 2015, 7 p.
Notice to Correct, issued Jan. 7, 2016, in U.S. Appl. No. 14/975,3030, filed Dec. 18, 2015, 2 p.

\* cited by examiner

BAR 1  BAR 2

BAR 1  BAR 2

BAR 1

ABSORBABLE COPOLYMERS WITH IMPROVED THERMAL STABILITY

CROSS-REFERENCE TO RELATED APPLICATION

This application is a continuation of U.S. application Ser. No. 14/975,303, filed Dec. 18, 2015, which claims the benefit under 35 U.S.C. § 119(e) of U.S. Provisional Application No. 62/094,723, filed Dec. 19, 2014, where each application is incorporated herein by reference in its entirety for all purposes.

BACKGROUND OF THE INVENTION

The present invention relates to absorbable copolymers with improved characteristics including thermal stability, molecular weight consistency, inherent viscosity retention following melt extrusion, as well as methods of manufacturing the improved absorbable copolymers. The present invention further relates to absorbable fibrous constructs which may be used for controlled drug delivery.

Previous work in the polymer field, such as U.S. Pat. No. 6,462,169 to Shalaby, discloses polyaxial block copolyesters containing high glycolide end-grafts. However, the polymers resulting from this disclosure lack various properties compared to the current disclosure, such as thermal stability, molecular weight consistency, and inherent viscosity retention following melt extrusion. Further, fibers made from the '169 disclosure lack the strength and toughness exhibited by fibers made from the polymers of the present disclosure. Moreover, the polymers disclosed by '169 are limited to polyaxial block structures synthesized in the solid state at 180 QC. The polymers of the '169 disclosure are synthesized in two steps that involve first synthesizing a prepolymer and then end-grafting to produce crystallizable end segments. The end segments are synthesized by reacting the pre-polymer with monomer at 180° C. until the reaction contents become solid, followed by continuing the reaction in the solid state at the same temperature for two more hours.

Additionally, U.S. Pat. No. 6,498,229 to Shalaby discloses high glycolide block copolymers synthesized in the solid state. The polymers disclosed by '229 are synthesized with higher amounts of catalyst than what is used to synthesize, for purposes of example only and not intended to be limiting, high glycolide polymers of the current disclosure. Specifically, polymers of '229 are synthesized with a monomer-to-catalyst (M/C) ratio of 60,000. The polymers resulting from the '229 disclosure are not only formed from a solid state synthesis using more catalyst but lack the thermal stability, molecular weight consistency, and inherent viscosity retention following melt extrusion characteristics of polymers made pursuant to the current disclosure.

Furthermore, the '229 reference is also limited to polymer compositions synthesized in a single step reaction. The polymers also contain less than 80% (and more than 20%) by mole of glycolide-derived repeat units. Furthermore, the two-step synthesis methods in '229 may have "fair-to-inadequate reproducibility." However, unexpectedly, and in contrast to '229 disclosure, the polymers of the current disclosure have demonstrated more than adequate reproducibility despite being synthesized by a two-step method.

Additionally, U.S. Pat. No. 6,342,065 to Shalaby discloses high lactide block copolymers synthesized in the solid state by a two-step method. However, the polymers resulting from the '065 disclosure lack the thermal stability, molecular weight consistency, inherent viscosity retention following melt extrusion, and the improved fiber strength of the polymers of the current disclosure.

Further, Zhao, U.S. Pat. No. 7,265,186, discloses multi-axis constructs with a hydrophilic core for star-shaped block copolymers. These cores are not hydrolytically degradable.

Meanwhile, Wang, U.S. Pat. No. 8,262,723, discloses implantable medical devices fabricated from branched/polyaxial polymers. Wang describes branched/polyaxial constructs, however, the polyaxial blocks are always present with a second and different polymer having the same chemical construction as the terminal blocks of the polyaxial block. The current disclosure provides discrete phases that do not constitute a blend of a polyaxial terminal block with a second polymer and a second phase comprising a prepolymer. The novel compositions disclosed herein form different discrete phases formed from blocks of the end graft and/or blocks of the prepolymer. Per the current disclosure, when a polyaxial may be present in combination with a second polymer having a same or similar composition as the terminal blocks of the polyaxial, the second polymer has a chain length and degree of polymerization that is twice the chain length and degree of polymerization of the terminal block of the polyaxial. Further, Wang fails to disclose flexible linking segments as disclosed herein.

Jakubowski, U.S. Pat. No. 8,569,421, describes polyaxial polymers with multiple axes. However, these compositions are not symmetrical and are intentionally designed to have unsaturated bonds distributed at particular locations along the polymer arms so that the polymers are more oxidatively stable. The Jakubowski constructs are not intended to be biodegradable/absorbable. Further, they are not specifically directed to implantable compositions.

Himes, U.S. Pat. No. 5,639,831, is directed to polyaxial block copolymers for different applications than the current disclosure. Moreover, it does not require the same chemical functionality and biocompatibility as the polymers of the current disclosure.

Accordingly, it is an object of the present invention to provide absorbable copolymers with thermal stability, improved molecular weight consistency, higher inherent viscosity retention following melt extrusion, and fibers made from the copolymers demonstrate increased strength.

SUMMARY OF THE INVENTION

The above objectives are accomplished according to the present invention by providing, in a first embodiment, an absorbable aliphatic polyester copolymer. The copolymer includes a polyaxial core, with at least three axes, and a pre-polymer. The at least three axes comprise polymeric chains. There is also at least one flexible linking segment. Further, at least one polymeric end graft is attached to each of the at least three axes, the end graft comprising repeat units derived from at least one cyclic monomer capable of crystallization.

In a further embodiment, the polyaxial core comprises crystallizable polymeric chain segments. Alternatively, the polyaxial core comprises amorphous chain segments. In another embodiment, the flexible linking segment and the crystallizable cyclic monomer share a common monomer. In another embodiment, the flexible linking segments are comprised of the same prepolymer as the polyaxial core and the same crystallizable cyclic monomer as the at least one polymeric end grafts.

Still further, the prepolymer may be a homopolymer, copolymer or terpolymer formed from the group consisting of L,L-lactide and D,L-lactide, glycolide, substituted glycolides, para-dioxanone, 1,5-dioxepan-2-one, trimethylene carbonate, epsilon-caprolactone, alpha-Angelica lactone, gamma-valerolactone and delta-valerolactone, or combinations thereof. Even further, the pre-polymer may be derived from ε-caprolactone, trimethylene carbonate, or a combination of the two. Further, the pre-polymer may be derived from glycolide, trimethylene carbonate or a combination of the two. In a still further embodiment, the copolymer comprises at least four distinct blocks including a central crystallizable core with at least three axes including crystallizable end blocks grafted to the at least three axes. Even further, the at least one crystallizable cyclic monomer may be selected from the group consisting of L,L-lactide and D,L-lactide, glycolide, substituted glycolides, para-dioxanone, 1,5-dioxepan-2-one, trimethylene carbonate, epsilon-caprolactone, alpha-Angelica lactone, gamma-valerolactone and delta-valerolactone, or combinations thereof. In another embodiment, the flexible linking segments may be derived from trimethylene carbonate, £-caprolactone, or a combination of the two. Still further, the polyester copolymer may comprise an absorbable barrier, web, mesh or fabric. Even still further, the copolymer may be formed into a warp-knitted mesh. Still further, the copolymer may include an absorbable polymeric surface coating for controlled drug delivery.

In another embodiment, a method for producing an absorbable aliphatic polyester copolymer is provided. The method includes charging a reactor with a monomer, an initiator, and a catalyst: the monomer to catalyst ratio is at least 25,000. The initiator may have at least one hydroxyl group capable of initiating ring-opening polymerization. The monomer may include at least one cyclic monomer. The reactor is heated to at least 100° C. The monomer may be stirred to form a homogenous mixture prepolymer, wherein weight of the prepolymer is greater than 10 kDa. A copolymer may then be formed with multiple amorphous prepolymer axes and crystalline end grafts emanating from each axis.

In a further embodiment, the catalyst may be stannous octoate. Other catalysts include $Sn(Oct)_2$, $Sn(OTf)_2$, dibutyltin(II)-2-ethylhexanoate ($Bu_2Sn(Oct)_2$), 4-(dimethylamino) pyridine (DMAP) Further, the initiator may be selected from the group consisting hydroxyl bearing small molecules, oligomers, polymers, and also inorganic and organic salts, or combinations of the above. Even further, the initiator may be selected from the group consisting of 1-decanol, 1,3-propanediol, trimethylolpropane, triethanolamine, 1,3,4-trihydroxy-2-butanone, glycerol or combinations of the above. In a further embodiment, the monomer may be a copolymer or terpolymer derived from lactide, trimethylene carbonate, and/or f-caprolactone. In a still further embodiment, the monomer may be a copolymer or terpolymer derived from glycolide, trimethylene carbonate, and/or f-caprolactone. In another embodiment, the monomer may be a substituted glycolide. In a further embodiment, a second charge of catalyst may be added to the reactor. In a still further embodiment, two independent temperature settings may be established during the reaction.

BRIEF DESCRIPTION OF THE DRAWINGS

The construction designed to carry out the invention will hereinafter be described, together with other features thereof. The invention will be more readily understood from a reading of the following specification and by reference to the accompanying drawings forming a part thereof, wherein an example of the invention is shown and wherein.

Figure 1:
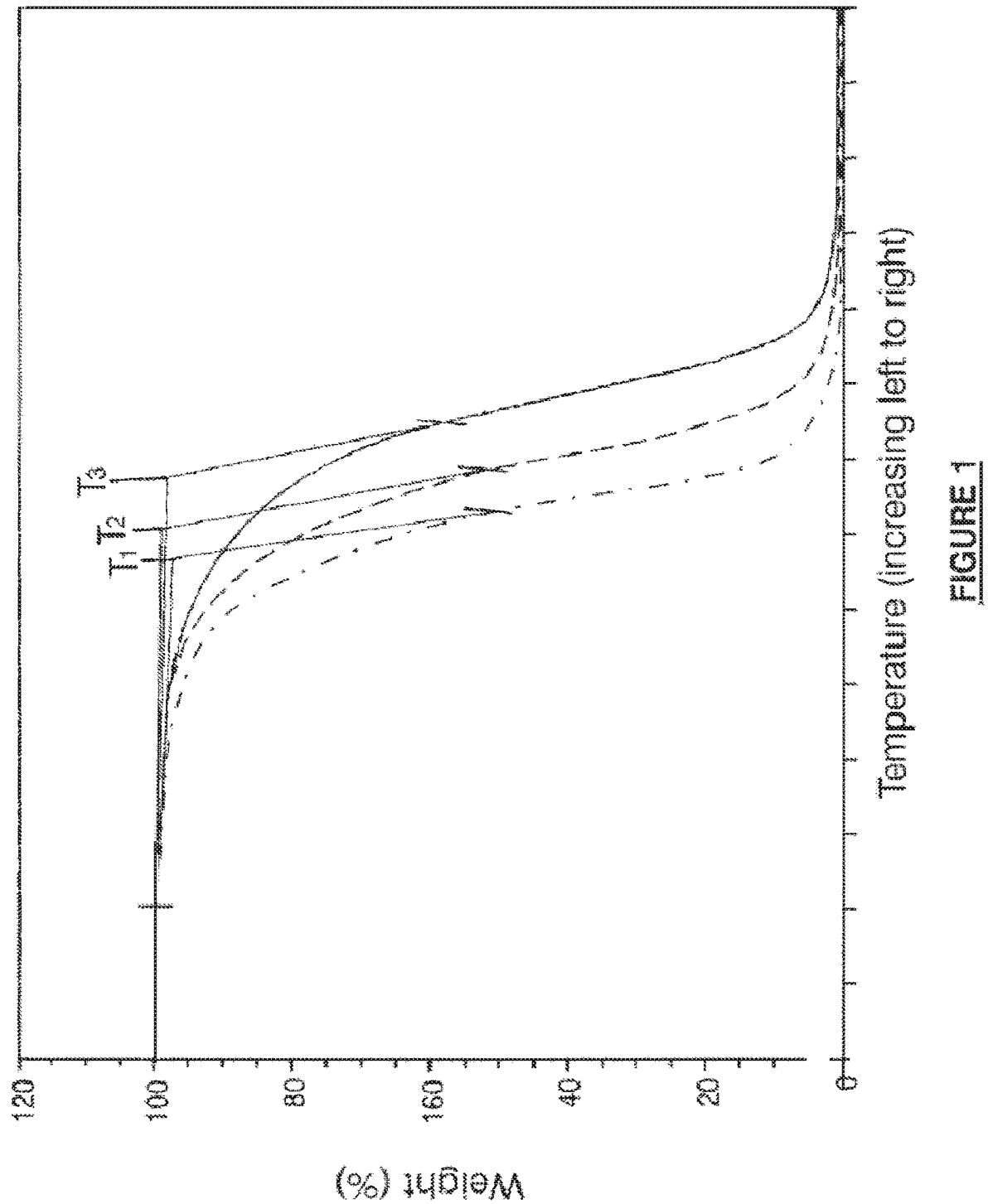
FIG. 1 shows thermogravimetric analysis (TGA) of polymers of the present invention.
Figure 2:
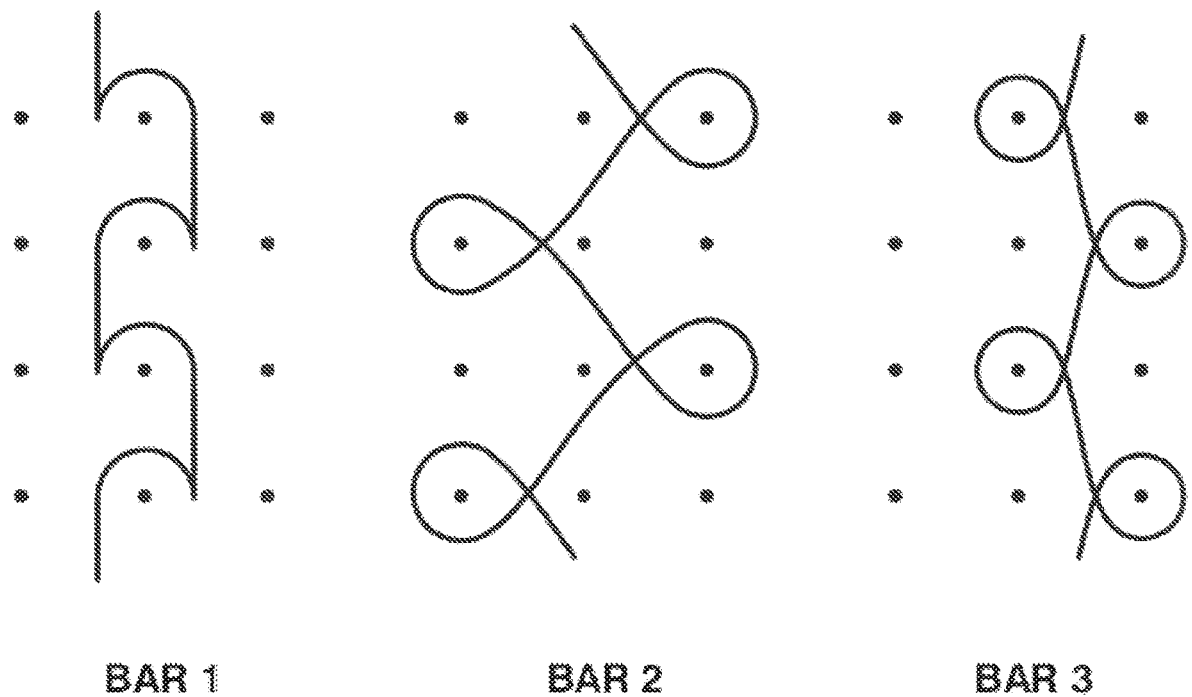
FIG. 2 shows one embodiment of the present disclosure in the form of a warp-knit 3-bar construction.

It will be understood by those skilled in the art that one or more aspects of this invention can meet certain objectives, while one or more other aspects can meet certain other objectives. Each objective may not apply equally, in all its respects, to every aspect of this invention. As such, the preceding objects can be viewed in the alternative with respect to any one aspect of this invention. These and other objects and features of the invention will become more fully apparent when the following detailed description is read in conjunction with the accompanying figures and examples. However, it is to be understood that both the foregoing summary of the invention and the following detailed description are of a preferred embodiment and not restrictive of the invention or other alternate embodiments of the invention. In particular, while the invention is described herein with reference to a number of specific embodiments, it will be appreciated that the description is illustrative of the invention and is not constructed as limiting of the invention. Various modifications and applications may occur to those who are skilled in the art, without departing from the spirit and the scope of the invention, as described by the appended claims. Likewise, other objects, features, benefits and advantages of the present invention will be apparent from this summary and certain embodiments described below, and will be readily apparent to those skilled in the art. Such objects, features, benefits and advantages will be apparent from the above in conjunction with the accompanying examples, data, figures and all reasonable inferences to be drawn therefrom, alone or with consideration of the references incorporated herein.

DETAILED DESCRIPTION

With reference to the drawings, the invention will now be described in more detail. Unless defined otherwise, all technical and scientific terms used herein have the same meaning as commonly understood to one of ordinary skill in the art to which the presently disclosed subject matter belongs. Although any methods, devices, and materials similar or equivalent to those described herein can be used in the practice or testing of the presently disclosed subject matter, representative methods, devices, and materials are herein described.

The present disclosure is directed to absorbable aliphatic polyesters with improved characteristics including thermal stability, molecular weight consistency, and inherent viscosity retention following melt extrusion. Further, fibers made from the polymers may exhibit increased strength. In one embodiment, the aliphatic polyesters of the present disclosure may include linear, crystalline block copolymers, such as di-block, tri-block and penta-block copolymers, which are synthesized from prepolymers that may be either amorphous or crystalline. In another embodiment, the aliphatic polyesters of the present disclosure may include linear, crystalline random or segmented copolymers, both of which are synthesized in a single reaction step without a prepolymer. In a further embodiment, the aliphatic polyesters of the present disclosure may include polyaxial, crystalline block copolymers (with at least three axes), which are synthesized from tri-axial prepolymers that may be either amorphous or semi-crystalline. In a still further embodiment, the aliphatic polyesters of the present disclosure may include polyaxial, crystalline segmented or random copolymers, both of which are synthesized in a single reaction step without a prepolymer. In a yet further embodiment, the polyester may be synthesized from cyclic monomers such as glycolide, lactide, para-dioxanone, trimethylene carbonate, e-caprolactone, morpholinedione, and mixtures thereof. In a still yet further embodiment, the polyester may be synthesized from an initiator compound containing from one to at least three hydroxyl groups capable of initiating ring-opening polymerization. In a further embodiment, the polyester may be a high glycolide copolymer that contains minor amounts of at least one additional monomer. By "high" it is meant that polymers may contain at least 50% by mole of glycolide-derived repeat units, at least 55%, 60%, 65%, 70%, 75%, 80%, 85%, 90%, 95%, or higher of glycolide-derived repeat units. Ranges of glycolide molar content are also envisioned by this disclosure including ranges of 50-60%, 60-70%, 70-80%, 80-90%, and 90-100%.

In a preferred embodiment, the high glycolide copolymer may be a highly crystalline, polyaxial block copolymer, wherein the block copolymer is synthesized in two steps. The copolymer may contain a tri-axial, amorphous prepolymer and high glycolide crystalline end grafts that emanate from the end of each of the three prepolymer arms. In a still further preferred embodiment, the high glycolide copolymer may be highly crystalline, polyaxial block copolymer, wherein the block copolymer contains a tri-axial, crystalline prepolymer and high glycolide crystalline end grafts that emanate from the end of each of the three prepolymer arms. In a still yet further preferred embodiment, the high glycolide copolymer may be a highly crystalline, polyaxial segmented copolymer, wherein the segmented copolymer is synthesized in a single reaction step that does not involve synthesizing a prepolymer. Further, since the segmented copolymer lacks a prepolymer, there are no distinct "blocks" within the polymer structure. In a further embodiment, the polyester may be a high lactide copolymer that contains minor amounts of at least one additional monomer. By "high" it is meant that polymers may contain at least 50% by mole of lactide-derived repeat units, at least 55%, 60%, 65%, 70%, 75%, 80%, 85%, 90%, 95%, or higher of lactide-derived repeat units. Ranges of lactide molar content are also envisioned by this disclosure including ranges of 50-60%, 60-70%, 70-80%, 80-90%, and 90-100%.

In a still further preferred embodiment, the high glycolide copolymer may be highly crystalline, polyaxial block copolymer synthesized in a two-step process involving synthesis of a crystalline prepolymer from caprolactone and trimethylene carbonate, followed by end-grafting the prepolymer with glycolide and caprolactone to yield the final block copolymer. This composition contains four distinct blocks: a central crystalline block with three axes and three crystalline end graft blocks emanating from each of the three chain ends of the central block.

The absorbable copolymers of the present disclosure may be formed by methods including ring opening polymerization conducted in the solid state and/or in the melt state. In a preferred method, the absorbable copolymers of the current disclosure may be synthesized in the melt, requiring that the reaction be conducted at a temperature above the melting temperature of the copolymer being synthesized. In another preferred method, the absorbable copolymers of the current disclosure may be synthesized, or allowed to finish reacting, in the solid state once the reaction product becomes too thick to stir and/or begins to crystallize. Ring Opening Polymerization ("ROP") conducted in the melt state and in a large reactor, such as an 8 CV reactor, is superior to solid state synthesis for forming the copolymers of the current application, especially when batch sizes greater than one kilogram are desired.

In one embodiment, a reaction may be performed by charging an 8 CV reactor with monomer and initiator, followed by heating the reactor to 100° C. with the system under Nitrogen (g), then stirring the molten monomer and initiator to create a homogenous mixture, and finally adding catalyst and increasing the reaction temperature above the melting temperature of the polymer being synthesized. The contents of the reactor will be stirred "in the melt", and the reaction will be driven to maximum conversion of the monomer to polymer. Then when maximum conversion has been reached, the molten polymer will be removed from the bottom of the reactor. This synthesis technique is commonly referred to as the "melt" technique. Meanwhile, solid state syntheses may limit the amount of polymer that can be synthesized in any one batch. However, by utilizing larger reactors that are suitable for ROP in the melt state polymers may be manufactured on a larger scale, such as in 7.5 kilogram batches in an 8 CV reactor, or much more than 7.5 kilograms for larger reactors. This is in comparison to solid state reactions conducted in smaller reaction vessels like 1-Liter kettles. Initiators for the reaction may include compounds with one to three hydroxyl groups capable of initiating ring-opening polymerization. Examples of which include, but are not limited, to 1-decanol, 1,3-propanediol, trimethylolpropane, triethanolamine, 1,3,4-trihydroxy-2-butanone and glycerol, or combinations of the above. Meanwhile, the preferred catalyst for these ROP reactions is stannous octoate. However, other catalysts as known to those of skill in the art may be employed. The polymers resulting from the methods disclosed herein may be linear or polyaxial copolymers in structure, and they may be either segmented or block copolymers. Thus, a prepolymer may or may not be used in the synthesis of the copolymers of the present disclosure.

FIG. 1 shows thermogravimetric analysis (TGA) of polymers of the present invention. Semicrystalline, linear block copolymers were tested. For purposes of example only and not intended to be limiting, a triblock copolymer with a middle block derived from a prepolymer and semicrystalline end grafts were tested. In one embodiment, the prepolymer comprised TMC and caprolactone and the end grafts comprised I-lactide and TMC.

As FIG. 1 illustrates, in the current disclosure increased thermal stability is obtained via a reduction in catalyst content. The catalyst amount can be described as the ratio of moles of monomer to moles of catalyst, and because moles of catalyst are in the denominator, a larger ratio means less catalyst. In FIG. 1, the three curves each represent a different polymer composition each with a different amount of catalyst (M/C of 20,000, 25,000, and 40,000 looking at the graph from left to right). Further, as FIG. 1 illustrates, each composition has a different temperature for the onset of degradation. Thus, thermal stability for the polymers of the current disclosure improves as the amount of catalyst decreases. E.g., T3 has the least amount of catalyst, T2 the next least, and T1 has the most catalyst of the polymers.

Thermogravimetric Analysis (TGA) was performed using a constant method of heating from 20° C. to 550° C. at a rate of 20° C./minute under a nitrogen environment. All samples were dried at room temperature and reduced pressure of less than 0.2 torr for one week. Under these constant conditions, the effects of residual monomer content and catalyst concentration on thermal stability were isolated. Four lots of unoptimized high lactide copolymer were analyzed by TGA to determine the onset temperature of degradation. Furthermore, 35 lots of the unoptimized high lactide copolymer were analyzed before and after extrusion to determine inherent viscosity (IV) retention after extrusion. The results are presented below in Table 1.

TABLE 1

Thermal and Shear Degradation Effects on Unoptimized High Lactide Copolymers

| Sample Name | Pre-extrusion IV (dl/g) | Post-extrusion IV (dL/g) | Percent Retention in IV (%) | Onset Temperature (° C.) |
| --- | --- | --- | --- | --- |
| Unoptimized High Lactide Copolymer Lots (Control) | 3.00 ± 0.29 | 1.62 ± 0.12 | 54.1 ± 4.47 | 319.72 ± 3.62 |

In one embodiment, a lactide-based copolymer (more specific) reaction is conducted at two independent reaction temperature settings wherein the high temperature alone results in lower conversion (<92% conversion) and the lower reaction temperature alone results in excessive reaction times (>150 hrs). The overall reaction with a combination of two independent reaction temperatures above and below the melt results in conversion >92% and a reaction time <150 hours. The first reaction temperature is above the melt wherein the reaction is completed in the molten state. The second reaction temperature is conducted in the solid state wherein the polymer is crystallized. The reaction temperature above and below the melt must differ by a minimum of 5° C., preferably 5-10° C., even more preferably 10-20° C., and even more preferably >20° C. than the reaction temperature in the solid state. The reaction temperatures were measured by the bath temperature with a thermocouple. Under these conditions, the polymer is reacted in a batch process wherein there is no change in the reaction vessel. Changes in vessel types present potential contamination such as the introduction of moisture.

Figure 9:
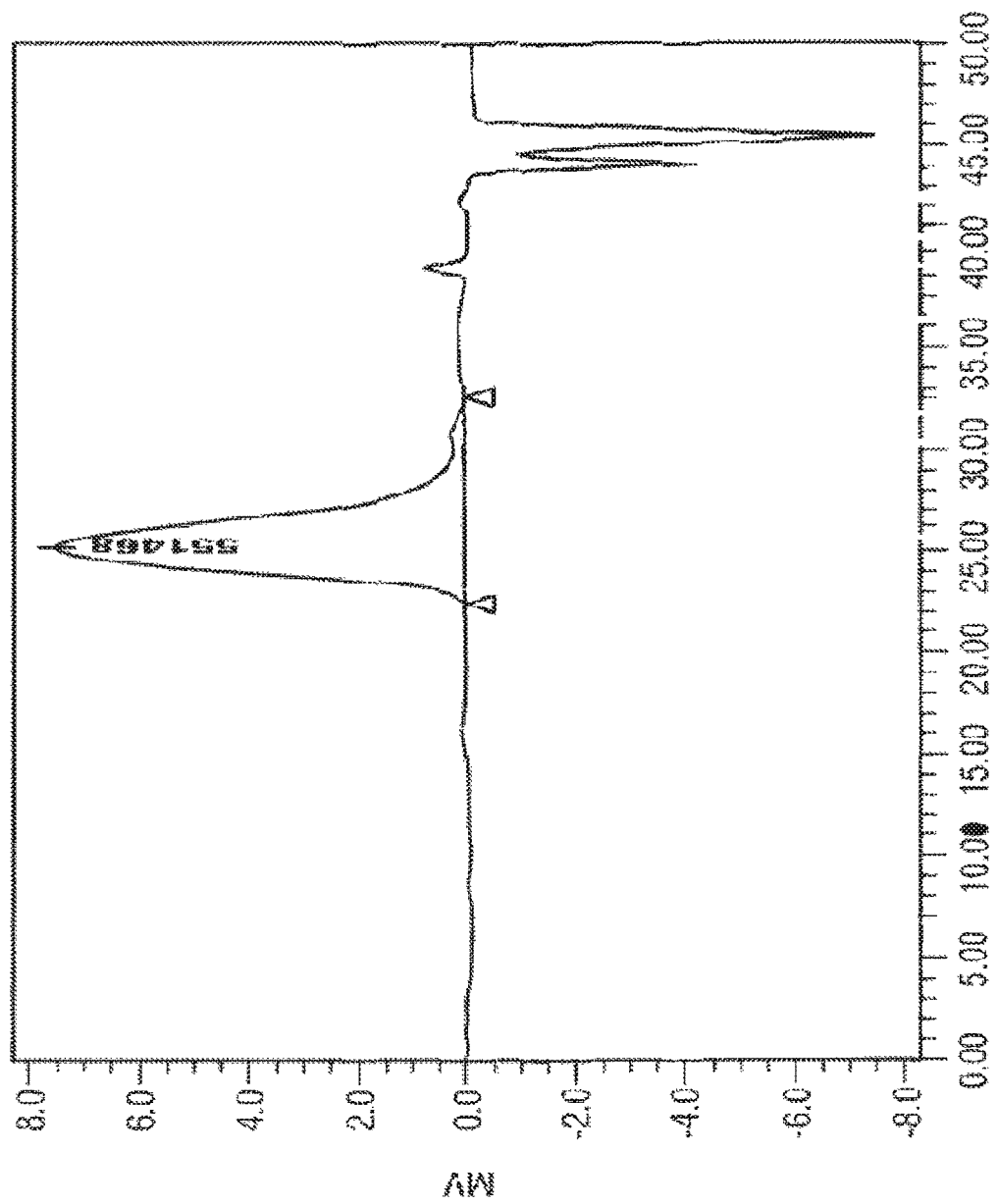
FIG. 9 shows incomplete mixing/nonhomogeneity via GPC analysis.

In another embodiment, the monomer to catalyst ratio of the prepolymer must be high enough to where the overall monomer to catalyst ratio after adding the second monomer (s) charge with >50% lactide for the crystalline segment is higher than an M/C of 25,000, more preferably >30,000, even more preferably >50,000, and even more preferably >100,000. Lower M/C values result in premature reaction of the prepolymer with the monomer(s) provided for end-grafting in subsequent reaction steps as described for methods of synthesis of block copolymers of the present disclosure. The premature reaction prevents complete dissolution of the prepolymer in the liquid monomer that is necessary for homogeneity prior to forming the terminal blocks/end grafted polymer chains onto the prepolymer. The resulting change is solubility hinders the complete dissolution of the prepolymer and therefore a nonhomogeneous polymer comprising a mixture of a block copolymer and residual, undissolved prepolymer that was not able to react with the monomer in the second charge. This result is confirmed by visual non-homogeneity or by GPC analysis as shown with a shoulder peak in FIG. 9. Optionally, more catalyst may be added to the reaction vessel following complete dissolution and mixing of prepolymer with the second charge, which would result in a decreased M/C. In reactions such as these where catalyst is provided in two or more steps during polymerization, it is necessary for the M/C to be greater than 115K, 125K, 150K, 175K, 190K, 200K, 215K. The prepolymer may optionally be reacted with additional monomer to form the flexible linking segment, followed by reaction with a third monomer or mixture of monomers to form the terminal blocks. In both the second and third grafting reactions, it is desired to have a consistent degree of polymerization for each polymeric arm of the block copolymer, as well as the same approximate degree of polymerization for the polymer chains of the bulk composition in the reactor. With respect to GPC analysis, multi-modal results are observed when there is essentially a blend of prepolymer that is unreacted or partially reacted with a block copolymer comprised of the prepolymer and terminal end-grafted blocks. The prepolymer is not consistent; some part reacts, some do not with a second charge of monomer. This results in a blended composition of different polymers, which may even be amorphous polymers distributed within the desired polymer.

Preferred catalysts for ring-opening polymerizations include organotin compounds such as Tin(II) 2-ethylhexanoate and dibutyltin oxide, but other alternatives include. Furthermore, suitable initiators for ring-opening polymerization include hydroxyl bearing small molecules, oligomers, polymers, and also inorganic and organic salts. The initiator may be in the form of a small molecule with an average molar mass less than 1000 grams per mole, or less than 500 grams per mole, or less than 300 grams per mole such that the molar mass of the initiator is comparable to the average molar mass of a single monomer (cyclic monomers, such as lactones and carbonates typically have average molar mass between 100 and 200 grams per mole). In some embodiments the initiator comprises a single hydroxyl or amine group, or two or more hydroxyl or amine groups, or at least one amine group in combination with one or more hydroxyl groups, such that the initiator may be in the form of monofunctional hydroxyl- or amine-bearing species, or a polyol or polyamine with two or more reactive groups, or a hydroxyl-amino compound comprising one or more hydroxyl groups and one or more amino groups. Combinations of suitable initiators as disclosed herein may be used in a single reaction to synthesize a mixture of different polymers having different configurations while still having the same total chemical composition of repeat units.

In some embodiments the catalyst may serve as the initiator for ring-opening polymerization of cyclic monomers, including but not limited to lactones, carbonates and morpholinediones. Non-limiting examples of suitable monomers include lactides, such as L,L-lactide and D,L-lactide, glycolide, substituted glycolides, para-dioxanone, 1,5-dioxepan-2-one, trimethylene carbonate, epsilon-caprolactone, alpha-Angelica lactone, gamma-valerolactone and delta-valerolactone. Additional monomers suitable for use in some embodiments include 5- and 7-membered cyclic esters, carbonates and amides which may optionally be present in combination (e.g. a cyclic amide-ester, also known as a morpholinedione).

Substituted glycolides referenced to in the present disclosure may display side groups other than a proton at one or both methylene (—CH2-) carbons. Non-limiting examples of substituents include the following: saturated hydrocarbons having at least two carbons, which may be linear or branched, and which may be functionalized; some functional groups require protection prior to ring-opening polymerization followed by deprotection once polymerization is complete; other functional groups do not interfere with the polymerization reaction and do not require protection/deprotection; some desirable functional groups may participate in the polymerization to cause secondary reactions such as branching off of the main polymer chain axis which allows for the formation of unique polymer structures, such as hyperbranched polymers.

Additional suitable substituents for modifying glycolides may include aromatic groups with at least one carbon separating the aromatic group(s) from the methylene carbon on the ring (to create separation between the aromatic ring and the reaction site on the ring in order to prevent a significant decrease in reactivity). Other useful substituents may include unsaturated hydrocarbons having one or more carbon-double bonds, wherein the unsaturation may be located terminally (i.e. vinyl end group) or internally on the hydrocarbon, and wherein the unsaturated hydrocarbon may be aliphatic or aromatic. Furthermore, halogens such as bromine and iodine may be used as suitable substituents—they may act as good leaving groups for secondary reactions during or following polymerization, and the halogens may be able to impart radiopaque character if the halogen atoms are present in high enough concentrations along a polymer chain.

Furthermore, the substituents described above may be present as a single substituent on a glycolide ring, or they may be present in various combinations. For example they may be found in duplicates and present on the same or opposite (para) carbons. Alternatively, two chemically different substituents may be present on the same ring, and the substituents can be present on the same carbon or on different carbons. Since the methylene carbons on glycolide exhibit sp3 hybridization, each of the two protons on a methylene carbon may be substituted as disclosed herein. Further, the same or different substituent may be found on the same carbon. Chirality of the substituted glycolide will be determined by the arrangement of substituent groups along the ring.

In another embodiment, the prepolymer must be heated to a minimum of 110° C., more preferably >115° C., even more preferably >120° C. and even more preferably >130° C. in order for dissolution into the second charge.

In a further embodiment, a glycolide based copolymer must have a monomer to catalyst ratio of the prepolymer high enough to where the overall monomer to catalyst ratio after adding the second monomer(s) charge with >50% glycolide for the crystalline segment is higher than an M/C of 90,000, more preferably >100,000, even more preferably >150,000, and even more preferably >200,000. High monomer to catalyst ratios in the prepolymer result in premature reaction of the prepolymer to the second charge and therefore change in solubility. The resulting change is solubility hinders the complete dissolution of the prepolymer and therefore an inhomogeneous polymer with a mixture of a block copolymer and residual, undissolved prepolymer that was not able to react with the monomer in the second charge. This result is confirmed by visual non-homogeneity. Optionally, more catalyst may be added to the reaction vessel following complete dissolution and mixing of prepolymer with the second charge, which would result in a decreased M/C. In reactions such as these where catalyst is provided in two or more steps during polymerization, it is necessary for the M/C to be greater than X in order to achieve complete dissolution and homogeneity.

In another embodiment, the prepolymer molecular weight must be greater than 10 kDa, more preferably >15 kDa, and even more preferably >20 kDa.

In another embodiment, the prepolymer molecular weight must be greater than 10 kDa, more preferably >15 kDa, and even more preferably >20 kDa, even more preferably >30 kDa, even more preferably >50 kDa, and even more preferably >60 kDa (include source). The molecular weight of the prepolymer is determined by GPC.

The developmental lots synthesized for the present disclosure used a reduced catalyst concentration. The temperature and time of the reactions were modified to account for this change. Due to lower catalyst concentrations and new reaction conditions, the optimized high lactide copolymers were expected to have decreased conversion and increased residual monomer content. The reaction conditions for each optimized lot are described in Table 2 below.

TABLE 2

Reaction Conditions for Control and Optimized High Lactide Copolymers

| Polymer Lot # | M/C Ratio | Reaction Temperature (° C.)/Reaction Time (hrs) |
|---|---|---|
| Control | 14,000 | 140/60 |
| 1d | 25,000 | 150/60 |
| 2d | 40,000 | 160/60 |
| 3d | 40,000 | 160/2.75 |
|  |  | 140/84 |
| 4d | 40,000 | 160/5.5 |
|  |  | 140/84 |

Table 3, below, shows data comparing area under the curve for tested polymers and monomers with gel permeability chromatographs (GPC). All optimized lots have high residual monomer content under the new reaction conditions. Lots 2d through 4d have notably higher residual monomer content. Lot 2d is capable of improved conversion (Lots 3d and 4d) by reacting at two independent temperature settings with one in the molten state followed by one in the solid state and a temperature difference of 20° C. This result is described in Table 3 by the reduced residual monomer in lot 3d and 4d.

TABLE 3

Residual Monomer Content for Post Synthesis
Optimized High Lactide Copolymers

| Lot Number | Residual Monomer (%) |
|---|---|
| 1d | 1.69 |
| 2d | 12.51 |
| 3d | 4.44 |
| 4d | 7.95 |

The post devolatilization molecular weight and residual monomer content results for the control and optimized lots are outlined in Table 4. The modified devolatilization procedure reduced the residual monomer content below the control values, and the average residual monomer content in the optimized lots was less than 1 weight percent. Both lots 1d and 4d, comprising high lactide block copolymers and described as SMC 22, had an I.V. that was out of the current specification of >2.4 dl/g. Furthermore, the POI decreased for each of the optimized lots with reduced catalyst concentration.

TABLE 4

Molecular Weight and Residual Monomer Results
for Optimized High Lactide Copolymers

| Lot Number | Mn (kDa) | Mw (kDa) | PDI | Residual Monomer (%) | Inherent Viscosity (g/dL) |
|---|---|---|---|---|---|
| Control | 298.7 ± 57.4 | 578.0 ± 29.7 | 2.01 ± 0.54 | 1.58 ± 0.35 | 3.00 ± 0.29 |
| 1d | 205.8 ± 30.9 | 362.5 ± 36.6 | 1.77 ± 0.10 | 0.45 ± 0.27 | 1.97 |
| 2d | 286.3 ± 72.1 | 439.1 ± 70.1 | 1.56 ± 0.16 | 0.74 ± 0.28 | 3.15 |
| 3d | 343.3 ± 10.6 | 581.0 ± 1.2 | 1.69 ± 0.06 | 0.70 ± 0.42 | 3.37 |
| 4d | 243.8 ± 11.8 | 397.1 ± 16.4 | 1.63 ± 0.07 | 0.57 ± 0.06 | 2.39 |

The melt flow index (MFI) results of the optimized and control lots are listed below in Table 5. MFI is commonly used to predict initial extrusion settings. Many properties of aliphatic polyesters affect the MFI, including polymer molecular weight, residual monomer content, moisture content, temperature, pressure, and catalyst concentration. The method implemented consisted of a constant temperature of 205° C. and constant weight of 3800 grams. In optimized lots 2d through 4d, catalyst concentration and drying conditions remained constant.

In these samples, the different MFI values were a product of variations in molecular weight and residual monomer concentration between lots. Typically, the melt viscosity is expected to directly relate to the polymer molecular weight (melt viscosity typically increases with increasing molecular weight). In addition, residual monomer content may act as a plasticizing agent to reduce melt viscosity. When comparing lot 4d to lots 3d and 2d, it is apparent that the molecular weights of lots 3d and 2d are higher than lot 4d, but the melt viscosities of lots 3d and 2d are lower according to MFI results. Thus, the lower monomer content in lot 4d appears to increase the melt viscosity by decreasing the plasticizing effect of monomer. In summary, the melt viscosity typically increases with an increase in molecular weight, but it has been observed here that residual monomer content, or lack thereof, results in an increase in melt viscosity for lower molecular weight polymers.

TABLE 5

Melt Flow Index Results for Optimized High Lactide Copolymers

| Lot Number | MFI (g/10 min) |
|---|---|
| Control | 12.17 ± 7.71 |
| 1d | 20.91 ± 1.17 |
| 2d | 6.92 ± 3.14 |
| 3d | 3.85 ± 0.40 |
| 4d | 2.68 ± 0.13 |

The results for the onset temperature of degradation are reported below in Table 6. Each polymer was dried under constant conditions. When comparing lot 1d to 4d, it is apparent that lot 1d has a lower onset temperature of degradation (326.5° C.) than lot 4d (347.8° C.). Both lots of polymer had similar residual monomer content, but lot 4d had less catalyst, with a monomer to catalyst ratio of 40,000 compared to 25,000 for lot 1d. In this example, an increase thermal stability for lot 4d is indicated by the increase in the onset temperature by 21.3° C. When comparing lot 4d to the control, lot 4d had significantly less catalyst and residual monomer, and the onset temperature of lot 4d increased by 28.1° C. relative to that of the control. A TGA graph of the control, lot 1d and lot 2d are illustrated in FIG. 1. The effect of increasing thermal stability is supported by the shift in the curve to the right, and thereby increasing the onset temperature of degradation.

TABLE 6

Onset Temperature of High Lactide Copolymer
Thermal Degradation Temperature

| Lot Number | Onset Temperature (° C.) |
|---|---|
| Control | 319.72 ± 3.62 |
| 1d | 326.5 |
| 2d | 343.8 |
| 3d | 341.3 |
| 4d | 347.8 |

TABLE 7

Onset Temperature of High Glycolide Copolymer's
Thermal Degradation Temperature

| Sample | Onset Temperature (° C.) |
|---|---|
| M/C = 35,000 | 342.2 |
| M/C = 114,000 | 357.1 |

Figure 6A:
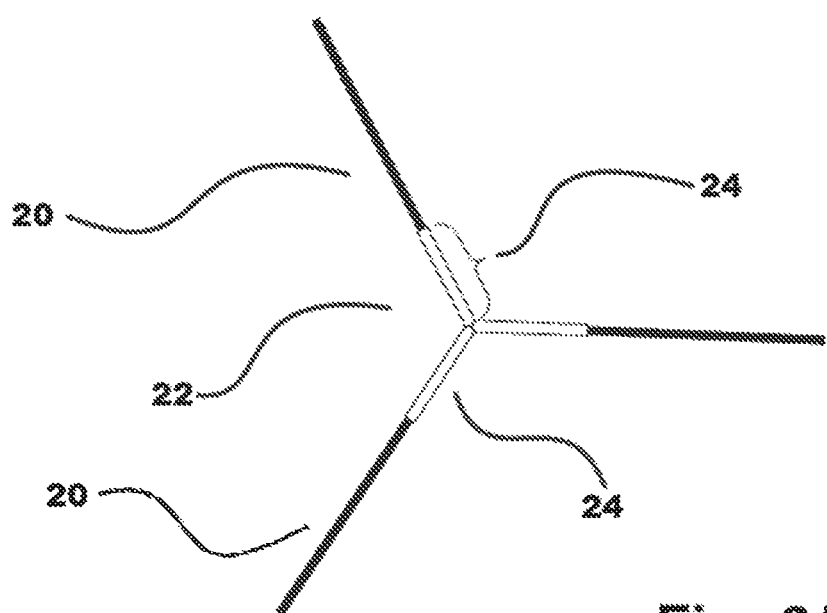
FIG. 6A illustrates a fully extended chain depiction of a semicrystalline, polyaxial block copolymer.
Figure 6B:
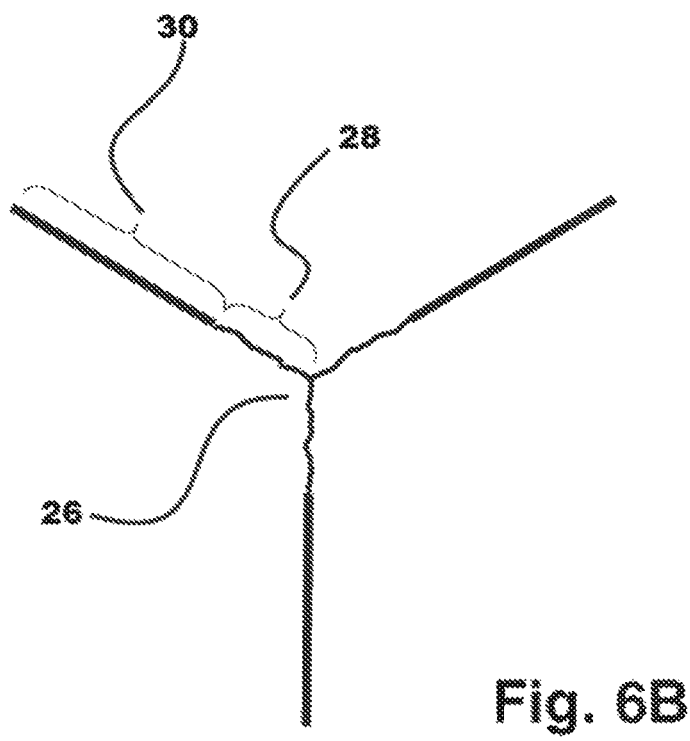
FIG. 6B shows an amorphous polyaxial core with polymeric amorphous arms having crystallizable end-grafts.

Multiple embodiments are possible via the current disclosure. For instance, FIGS. 6A and 6B illustrate two embodiments of the present disclosure. FIG. 6A, shows a fully extended chain depiction of a semicrystalline, polyaxial block copolymer wherein both the end graft and interior pre-polymer derived segments are crystallizable. 6A shows one embodiment of a semicrystalline end graft 20 of a polyaxial block copolymer 22 and semicrystalline prepolymer 24. In an alternative embodiment, FIG. 6B shows another embodiment of the disclosure. 6B shows an amorphous (incapable of crystalizing) polyaxial core 26, comprising three polymeric amorphous arms 28 each having a crystallizable, terminal end-graft 30.

Figure 7A:
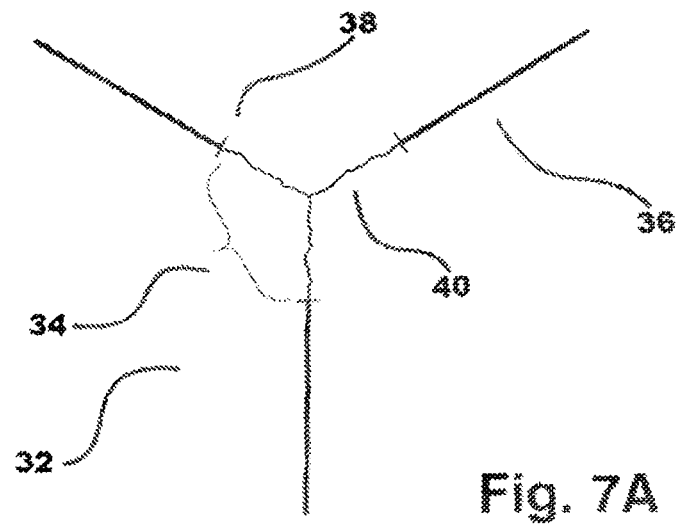
FIG. 7A shows a polyaxial block copolymer without a flexible linker connecting prepolymer to end graft.
Figure 7B:
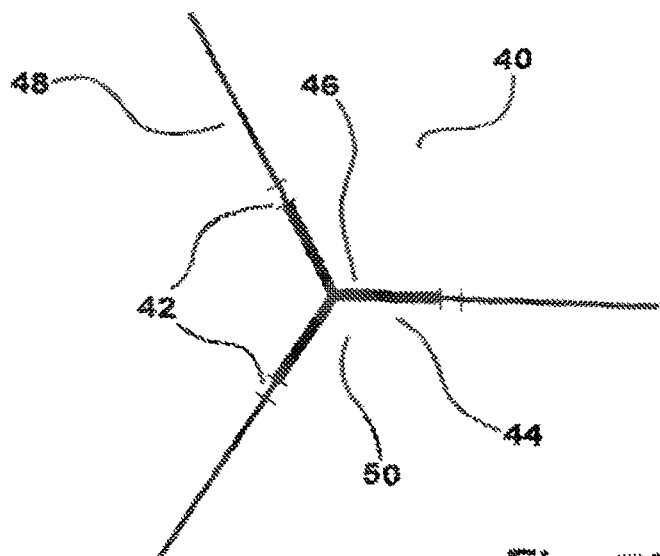
FIG. 7B shows a polymer construct with flexible linkers pre-polymer and end graft.

FIGS. 7A and 7B illustrate two further alternative embodiments of polymer constructs of the present disclosure. With respect to 7A and 7B, the illustrated prepolymers may be amorphous or crystallizable. FIG. 7A, shows a polyaxial block copolymer 32 without a flexible linker connecting prepolymer 34 to end graft 36. Cross mark 38 represents the junction between prepolymer 34 and end-graft 36, as well as represents the fully extended, theoretical conformation of arm 40 of prepolymer 34. FIG. 7B, shows a polymer construct 40 with flexible linkers 42 between block 44 derived from pre-polymer 46 and end graft 48 with core 50 derived from prepolymer 46, wherein core 50 may be crystallizable or amorphous. End grafts 48 may be amorphous or crystallizable. Flexible linker 42 has a minimum of 10 repeat units and may be derived from TMC in combination with other monomers described herein.

Figure 8:
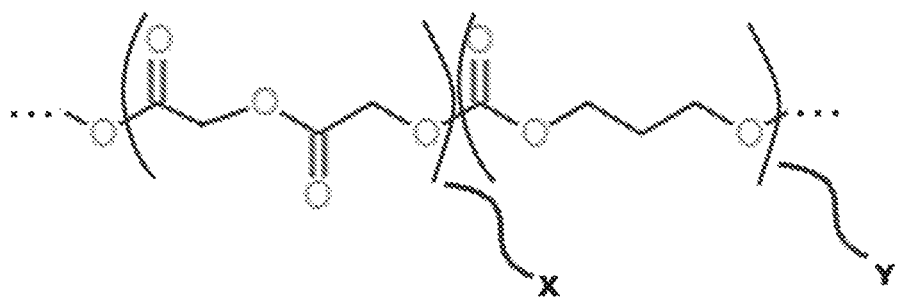
FIG. 8 illustrates the residual prepolymer after mixing and reacting the second charge using a prepolymer with a high catalyst concentration.
Figure 10:
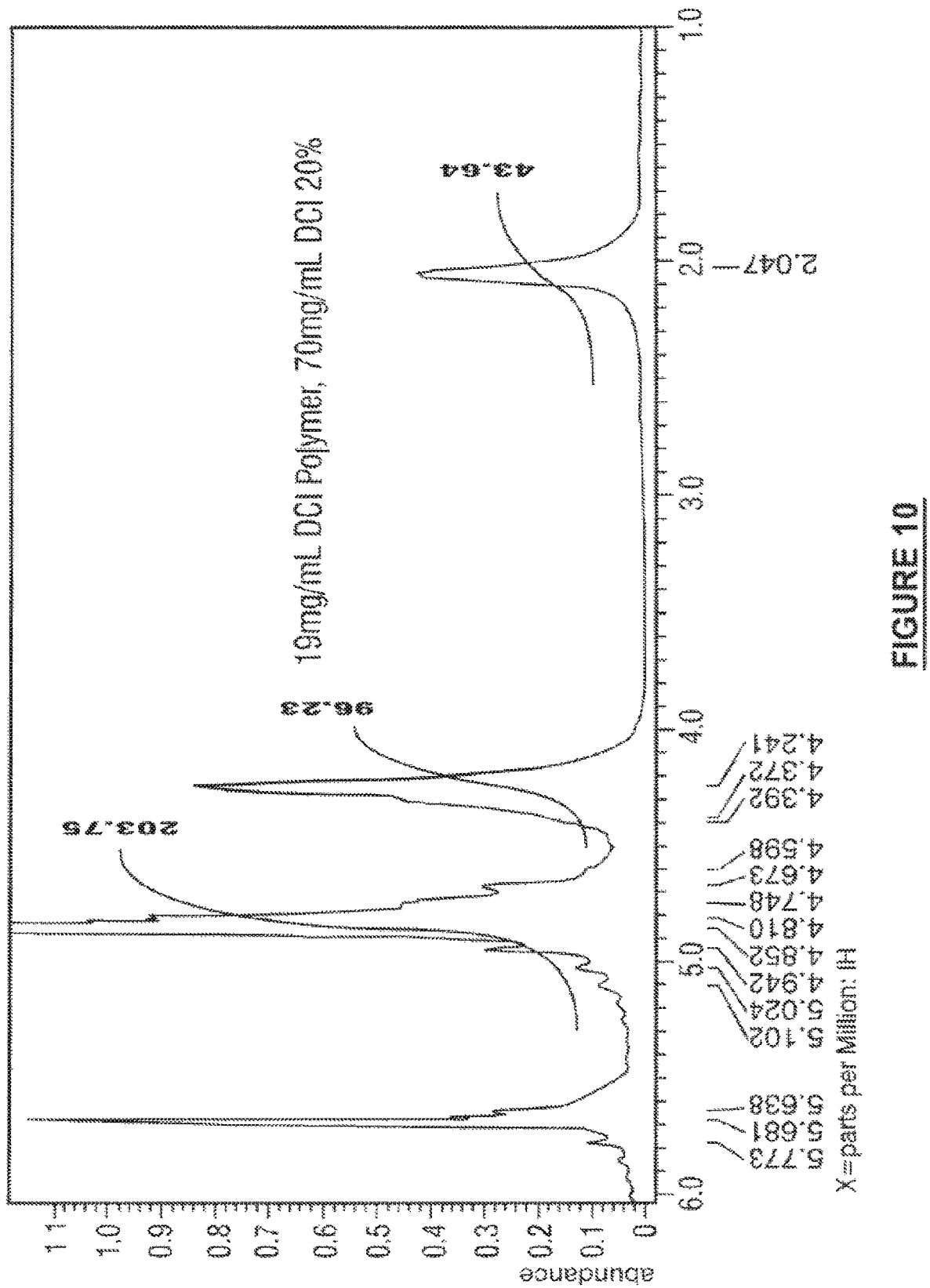
FIG. 10 illustrates an analysis of a polymer of FIG. 8.
Figure 11:
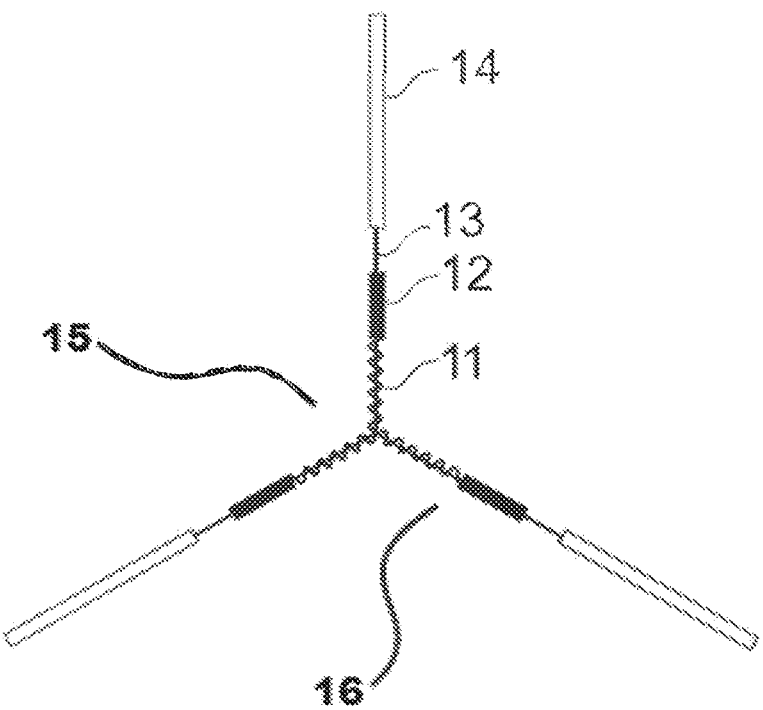
FIG. 11 illustrates a polymer of the current disclosure.

FIG. 8 depicts the chemical structure of repeat units that form a copolymer derived from glycolide and trimethylene carbonate (the copolymer represented by Elements 11, 12 and optionally 13 in FIG. 11). Analysis of one embodiment of the polymer of FIG. 8 is shown in FIG. 10. X represents a glycolide derived repeat unit and Y is a trimethylene carbonate derived repeat unit. In one embodiment, the respective molar ratios for the chemical structure is X+Y=1.0, X is approximately 0.333 and Y is approximately 0.667. As indicated in the figure, approximately 33 and 67% (by mole) of the repeat units are derived from glycolide and trimethylene carbonate, respectively.

The abbreviated polymeric structure represented in FIG. 8 and depicted on a larger scale in FIG. 11 may be synthesized in bulk or in solution, wherein the reaction is performed in the presence of initiator and catalyst, and optionally in combination with an inert organic solvent for solution polymerization. In a preferred embodiment the polymer is synthesized in bulk by ring-opening polymerization using a polyol initiator and Tin(II) 2-ethylhexanoate as the catalyst. Preferably the polyol has three or more reactive hydroxyl groups so that polymerization may result in a polymer having a star configuration with three or more distinct polymeric arms (wherein the exact number of polymeric arms or chains is equal to the number of reactive hydroxyl groups presented by the initiator). It is desirable for the polyol to exhibit symmetry and for the hydroxyl groups to have the same or very similar reactive rates, which will help to ensure that similar chain lengths are obtained for each polymeric arm (as depicted in FIG. 11). Triethanolamine is one example of a suitable polyol for synthesizing the three-arm, star copolymer depicted in FIG. 11.

FIG. 11 identifies terminal block 14 of one of at three arms 11 of a polyaxial block copolymer 15 as well as prepolymer segment 12 and flexible linker 13. In one embodiment, the terminal block 14 preferably formed entirely of glycolide-derived repeat units so that terminal blocks may form highly crystalline physical cross-links with terminal blocks of other star block copolymers. In contrast, prepolymer 16 may be formed from prepolymer segment 12 and flexible linker 13. Prepolymer 16 is intended to be elastomeric and should exhibit minimal or preferably no crystallinity. Flexible linking segment 13 may covalently link prepolymer segment 12 with the terminal block 14 on each arm 11. Flexible linker 13 is preferably a short linking segment of poly(trimethylene carbonate) that is entirely amorphous. Meanwhile, arms 11 and prepolymer segment 12 are both poly(glycolide-co-trimethylene carbonate), but, in one embodiment, arms 11 may contain a higher percentage of glycolide derived repeat units than prepolymer segment 12. Due to the differences in reaction rates of glycolide and trimethylene carbonate (glycolide reacts faster), the chemical composition of the prepolymer should decrease in glycolide content moving outward along the polymer chain until the terminal poly(glycolide) block is reached. Thus, when synthesis is initiated, both glycolide and trimethylene carbonate react until all the glycolide is reacted and only trimethylene carbonate remains to react.

As the amount of glycolide dwindles during the progress of the reaction, the segment represented by prepolymer segment 12 is synthesized, and if significant amounts of trimethylene carbonate remain then linking segment 13 may form in the first reaction step without the need for addition of more trimethylene carbonate to the reaction vessel. This situation is more likely to occur when the prepolymer is synthesized in the presence of less catalyst, as is preferred and taught by the present disclosure, and also this disparity in composition along the polymer chain is more likely to be observed when reactions are performed at low temperatures when differences in reaction rates of monomers are more apparent.

However, when higher reaction temperatures are used during prepolymer synthesis, a greater degree of randomization occurs such that the glycolide is distributed more evenly. It may then be necessary for additional trimethylene carbonate to be added to the reaction vessel and for a second reaction step to be performed in order to synthesize the flexible linking segment indicated by linking segment 13. The final reaction step in either of these two different scenarios involves addition of glycolide to the reaction vessel in order to graft glycolide onto the prepolymer and form the terminal blocks on all three polymeric chains. In order for this polymerization to be successful it is necessary to use minimal catalyst (preferably a molar ratio of total monomer to catalyst greater than 150,000 is necessary, but it is more preferable to employ higher monomer to catalyst ratios, such as 200,000), especially when the percentage of prepolymer within the final polymer is intended to be high, as is the case in FIG. 11 where the prepolymer may account for greater than 30-45% by weight of the total polymer (preferably 35%), and when the final reaction step requires complete dissolution of the prepolymer in molten glycolide before the temperature is increased to synthesize the terminal block. In a two-step reaction, elements 11, 12, and 13 are considered the prepolymer. In a three step reaction elements 11 and 12 represent two different regions of different compositions in the prepolymer based on the differences in reaction rates. In both cases, a two-step and a three step reaction, element 13 is considered the flexible linker.

Figure 12:
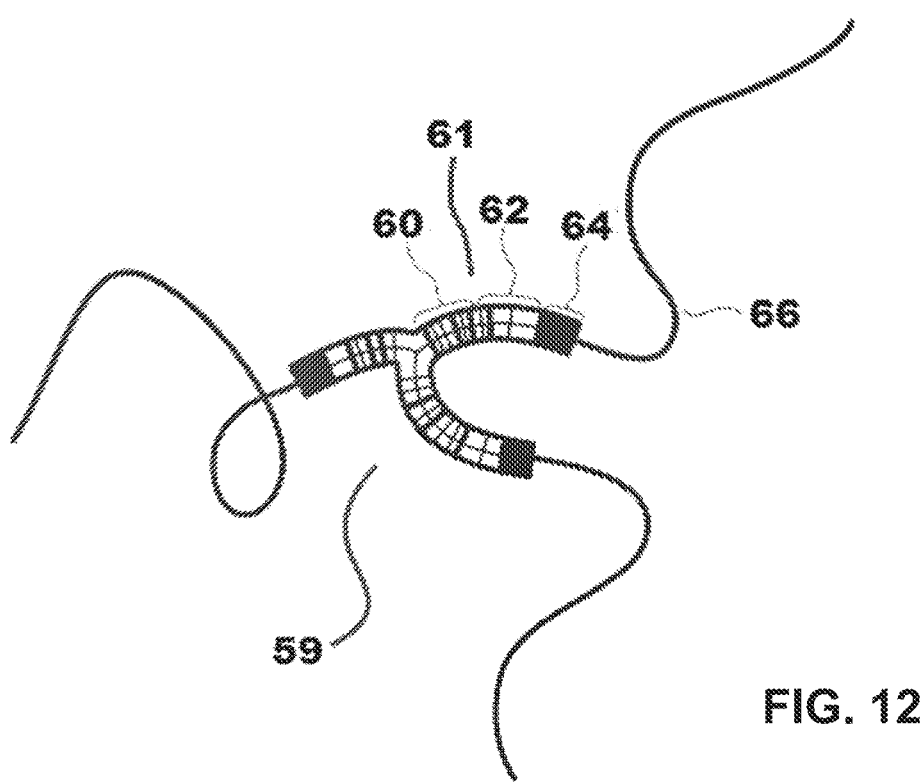
FIG. 12 illustrates an alternative embodiment of a polyaxial block copolymer comprising multiple segments.

FIG. 12 illustrates an alternative embodiment of a polyaxial block copolymer 59 comprising multiple segments. Segmented prepolymer 61 is comprised of random region 60 and transition 62. 60 and 62 illustrate two different regions in the prepolymer where, in one embodiment, most of the glycolide units are contained (60) and transition 62 shows where less glycolide repeat units formed predominately from slower reaction rate. Flexible linker 64 may be formed in a separate reaction step following synthesis of segmented prepolymer 61. End graft 66 may optionally be a high glycolide or high lactide terminal block.

Figure 13:
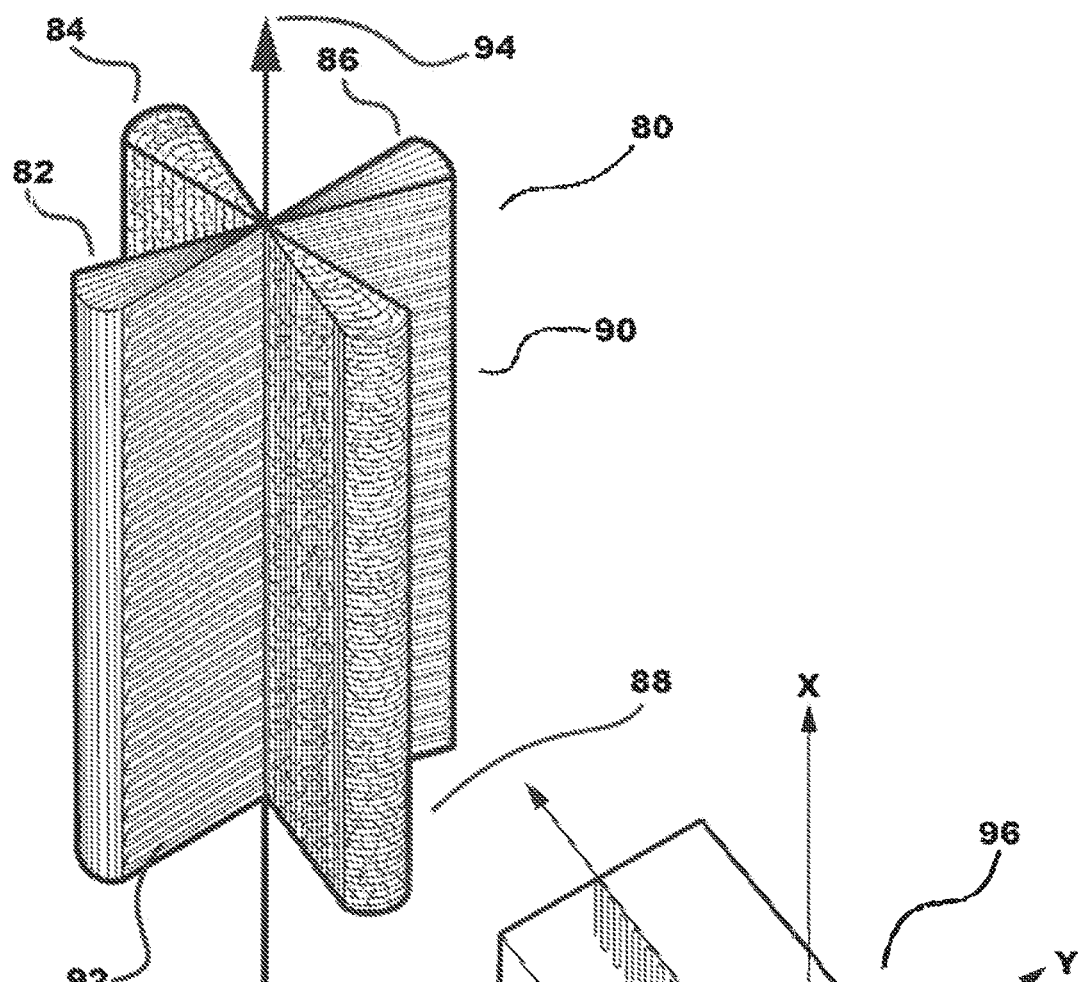
FIG. 13 shows four arm polyaxial copolymer oriented along an axis.

FIG. 13 shows four arm polyaxial copolymer 80 comprising arms 82, 84, 86, and 88. All four arms 82, 84, 86, and 88 comprise microstructure 90. Arm 82, in one embodiment, is a single arm of a polyaxial copolymer having four arms. Arm 82 maybe crystalline lamella oriented vertically comprised of a multitude of individual arms of the same composition 92. Arms 82 and 86 may be crystalline and 84 and 88 may be amorphous. 82 and 86 as well as 84 and 88 may have variable "widths" so that there is variable space between the arms. The chemical composition of opposing arms in FIG. 13 is substantially the same. FIG. 13 depicts a 4-arm polyaxial star polymer comprised of two types of polymeric arms—amorphous and semicrystalline. The 4 arms are oriented about central vertical axis 94 extending through the center of copolymer 80.

Figure 14:
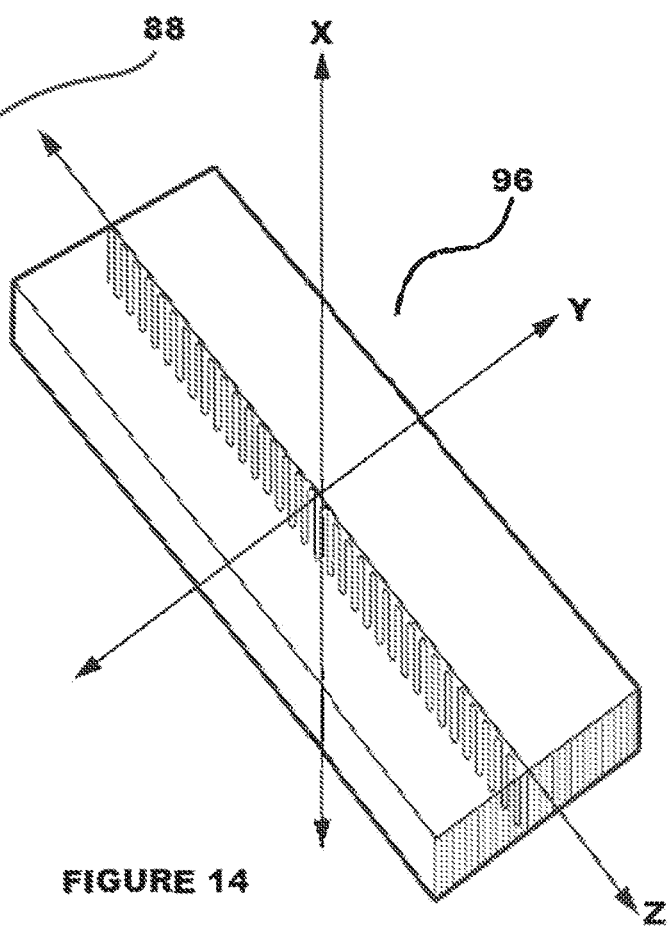
FIG. 14 is an excerpt view of FIG. 13 showing polymer chain folding of an exemplary arm that results in a chain-folded crystal.

FIG. 14 is an excerpt view of FIG. 13 showing polymer chain folding of an exemplary arm 96 that results in a chain-folded crystal. Thus, semicrystalline arms 82, 84, 86, and 88 of FIG. 13 reptate parallel or nearly parallel to the Z-axis as shown in FIG. 14, and outwardly from the Z-axis as the crystalline lamellae form. Additional 4-arm star polymers "stack" vertically and contribute to crystalline growth. The vertical integration of polymer chains results in vertical stacking and growth of crystalline domains along the Z-axis as depicted in FIG. 13. Further, the amorphous domain forms from a combination of chains extending outward from the Z-axis and connected to the crystallizing polymer chains, along with chains exiting the crystalline lamellae to entangle with the amorphous phase, which sometimes is followed by reentry into the crystalline microstructure, forming "loops" on lamellae surface associate with each other to form an organized conformation where each of the two similar arms are located opposite one another in the same plane.

Figure 15:
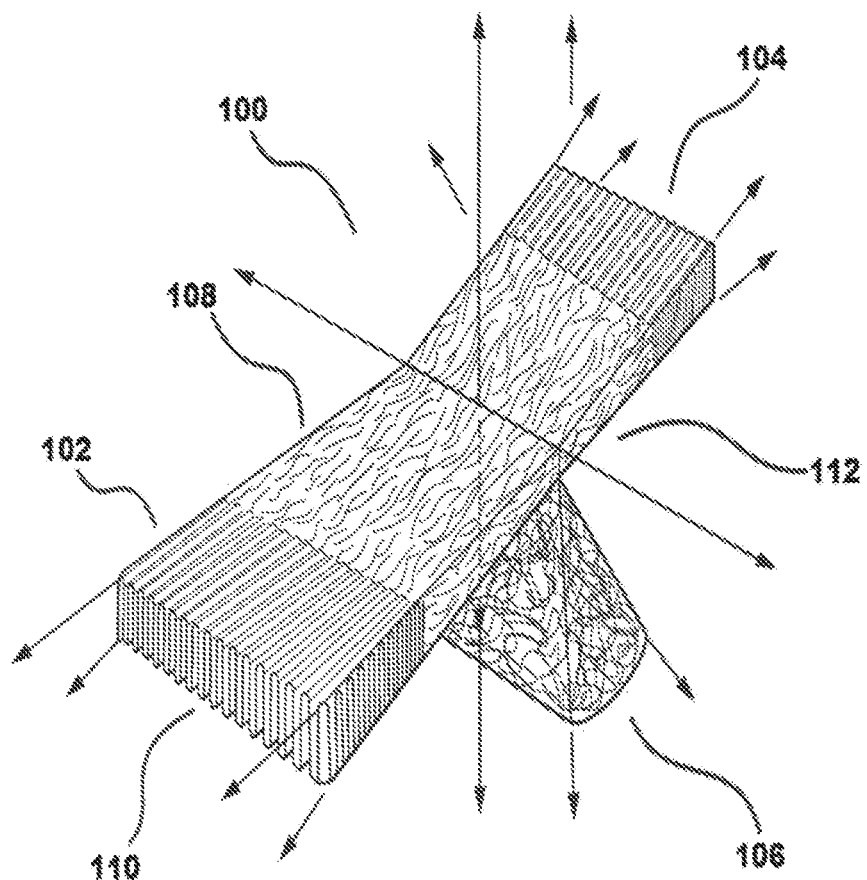
FIG. 15 illustrates an asymmetric polyaxial copolymer.

FIG. 15 illustrates an asymmetric polyaxial copolymer 100. In the illustrated embodiment two arms, 102 and 104, are chemically similar in composition while the third arm 106 is different in chemical composition. Arm 102 is comprised of internal amorphous block 108, formed as one arm of prepolymer 112, and external semicrystalline block 110 covalently bound thereto. Arm 106, which may be formed in a different reaction step than arms 102 and 104, may be formed in a first reaction step followed by a second reaction step to form arms 102 and 104. Alternatively, arm 106 may be formed as part of an initial reaction step wherein arms 102, 104 and 106 are chemically similar in composition. For instance, a two-step reaction may be employed to form a three arm amorphous prepolymer and one terminal hydroxyl group may be protected with, or optionally secured to a surface, prior to the second reaction step involving ring-opening polymerization to end graft terminal crystallizable blocks onto the two unprotected prepolymer arms.

Figure 16:
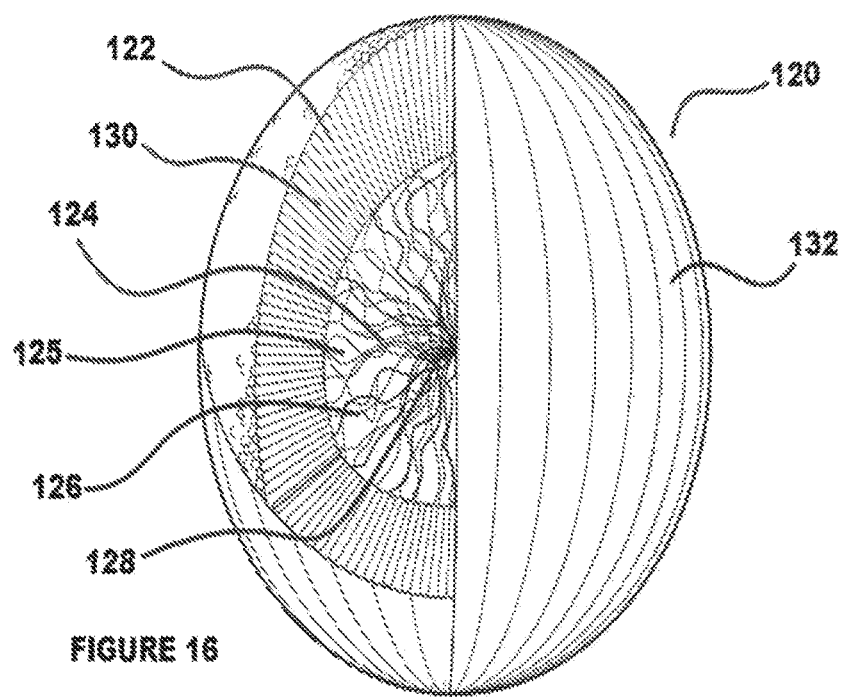
FIG. 16 illustrates a hyper-branched microstructure polymer.

FIG. 16 illustrates a single microstructure 120 depicting an individual polymer 122 that may be considered hyperbranched. Core 124 is formed by unoriented, amorphous, disordered polymeric chains 126 initiated at central location 128, essentially or substantially the center of microstructure 120, wherein disoriented polymeric chains 126 transition to external semicrystalline blocks 130. Blocks 130 may crystalize as illustrated in FIG. 14 by forming a chain folded crystal structure. The microstructure 120 of FIG. 16 may be used as a drug delivery system via the large void volume 125 of chains 126 allowing for dispersal of a bioactive agent, not shown, within the structure of chains 126. The size of the bioactive agent and concentration that may be loaded into the core 124 is dependent upon the number of polymer chains 126 that directly influence the totally available void volume that may be occupied by a bioactive agent. External shell 132, through chain folding of semicrystalline blocks 130, forms a tough, protective shell that acts as a protective layer for the void 125 and bioactive agent dispersed therein. The bioactive agent may be contained substantially within void 125 until shell 132 sufficiently degrades to allow sufficient porosity for diffusion of the bioactive agent through shell 132. Shell 132 may be designed to allow for initial bioactive release followed by increase bioactive release as shell 132 further degrades. It is preferred that defects in shell 132 be avoided in order to provide for protection of void 125. In a preferred embodiment, a single monomer may be used to synthesize terminal blocks 130 to allow for a uniform crystal structure. Multiple microstructures 120 may be employed together and overlap one another at shell 132 to form a crystalline domain between adjacent microstructures 120. Microstructures 120 may be formed into a film or used as individual spheres to allow for bioactive agent dispersal in a desired form over a desired time span.

In other preferred embodiments it is desired to form different polymer configurations, such as linear (unidirectional and bidirectional), multi-axial, star, branched, graft, comb, brush, circular and combinations thereof. However, the same concept of utilizing minimal catalyst is still necessary because it is needed to improve the thermal stability of copolyesters (in addition to facilitating homogenous mixing of prepolymer with the monomer(s) for the second/final reaction step) so that they may be processed at temperatures above the melting point of the polymer without causing extreme or significant degradation.

Absorbable fibers may be made from the polymers of the present disclosure via melt extrusion and electrospinning techniques as known to those of skill in the art. These fibers may be formed into solid constructs such as barriers, webs, meshes, or fabrics (woven or nonwoven), via methods as known to those of skill in the art. Alternatively, partially-absorbable constructs can be formed by combining absorbable polymers, and fibers derived therefrom, with nonabsorbable fibers derived from materials such as polyurethane, polypropylene, polyethylene, polyether ether ketone (PEEK), and polyethylene terephthalate.

In one embodiment, meshes may be constructed by warp-knitting and weft knitting. Specific knitting patterns may be chosen depending on the mechanical strength requirements for the particular medical application. Different techniques for forming fibrous constructs can also be combined in unique ways to create hybrid constructs. For instance, one can electrospin onto a warp-knit mesh to give it an electrospun surface or layer. Indeed, the polymers of the current disclosure are suitable as medical grade polymers for incorporation into various medical devices such as absorbable, or partially absorbable, meshes, pouches, containers, barriers, support structures, etc., that may be formed from the polymers of the present disclosure.

For instance, FIG. 2 shows one embodiment of the present disclosure where a warp-knit 3-bar construction may be employed. Three bar patterns may provide advantages with respect to enhanced dimensional and mechanical properties and enhanced stability particularly in the weft direction. Moreover, three bar patterns typically produce "heavier" fabrics. In one embodiment, a fabric made using a warp knit 3-bar construction may be employed for sealing applications. In one embodiment, a three bar constitution of Bar 1: 1-0-0/0-1-1, Bar 2: 2-3-2/1-0-1, Bar 3: 1-0-1/1-2-1 may be used.

Figure 3:
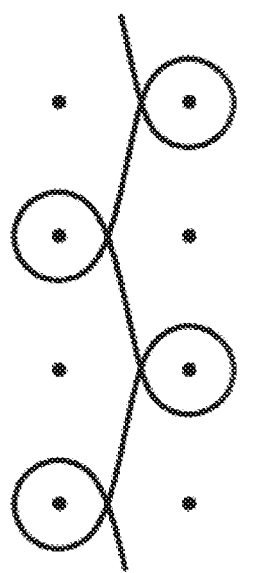
FIG. 3 illustrates one embodiment of the disclosure in the form of a Tricot warp-knit 2 bar construction.
Figure 3:
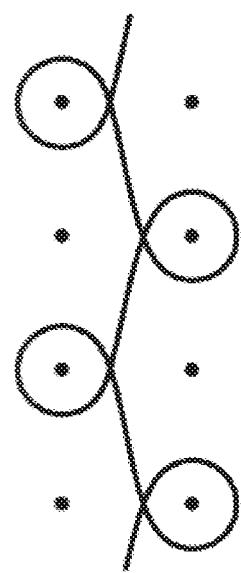

FIG. 3, meanwhile, illustrates one embodiment of the disclosure wherein a warp-knit 2 bar construction may be employed. In one embodiment, a Tricot fabric may be produced. Tricot has a simple construction and provides a light-weight fabric with short underlaps. In one embodiment, a 2 Bar construction may be employed comprising Bar 1: 1-2/1-0 and Bar 2: 1-0/1-2.

Figure 4:
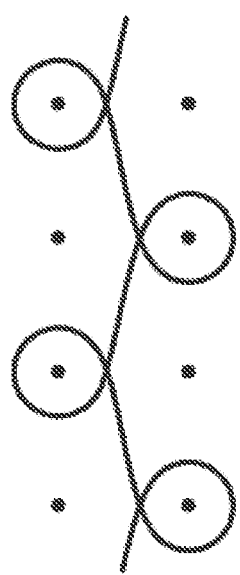
FIG. 4 shows one embodiment of the disclosure in the form of a warp-knit 2 bar "Sharkskin" construction.
Figure 4:
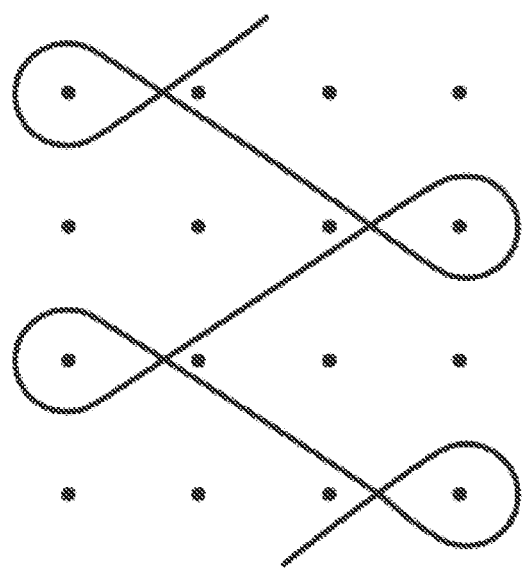

FIG. 4 shows another warp-knit 2 bar construction known as "Sharkskin." Sharkskin is a simple 2 bar construction, but it has a longer shagging distance that results in increased stability and increased areal density. Furthermore, the Sharkskin pattern demonstrates reduced shrinking potential. Thus, it provides a more rigid and stable structure. Furthermore, the surface texture of the Sharkskin construction is "rough" and can be used for medical applications where it is desired to create adhesions. In one embodiment, the a 2 Bar construction may be employed wherein Bar 1: 1-2-2/1-0-0 and Bar 2: 1-0-1/3-4-3.

Figure 5:
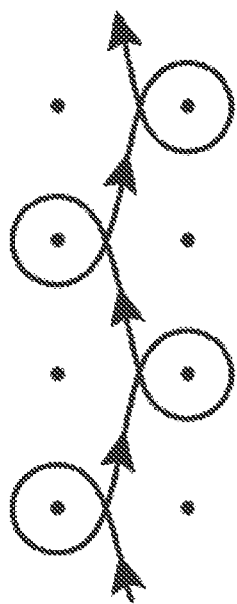
FIG. 5 illustrates another embodiment of the disclosure in the form of a half-tricot pattern.

FIG. 5 illustrates a half-tricot pattern that may be employed with the current disclosure. The half-tricot pattern results in a low areal density construction thereby providing a very light construct. While not as strong as tricot, it is easier to make, requires less material, and has a simple construction. In one embodiment, a construction may be employed where bar notation is 1-2/1-0. This is an example of a half-tricot pattern wherein the "1-2" means the guide bar overlaps as it moves right to left for one needle from position 1 to 2. "1-0" indicates yarn is fed left to right to the needles.

FIGS. 6A and 6B illustrate multi-axial structures for absorbable block copolymers comprising a pre-polymer that may be either amorphous or crystallizable, and also structures that comprise a flexible linking segment between the polymeric axes derived from the pre-polymer and the end-grafted terminal blocks. Suitable flexible linking segments may be derived from trimethylene carbonate and epsilon-caprolactone, optionally in combination. If epsilon-caprolactone is chosen for the flexible linking segment then it is necessary to ensure that the segment remains amorphous and that the chain length is not above the threshold for crystallization of caprolactone. In one preferred embodiment, the pre-polymer is derived from glycolide and trimethylene carbonate and is amorphous, and the flexible linking segment is derived from trimethylene carbonate, and the end-grafted blocks are derived from glycolide. Optionally, the flexible linker is formed by result of reaction parameters that allow for excess trimethylene carbonate to remain during a first polymerization reaction that forms the pre-polymer, such that after the pre-polymer forms, the remaining trimethylene carbonate can react to form the flexible linker. A second method of forming the linker is to react the pre-polymer at elevated temperature to ensure randomization of the pre-polymer and no segmentation of trimethylene carbonate at the terminals of the pre-polymer, followed by addition of more trimethylene carbonate to the reaction vessel to form the linking segment. The glycolide is added to the reaction vessel to form the end grafted blocks after the trimethylene carbonate has been reacted to completion. Properties of polymers made according to this procedure are provided in Table 8:

| BATCH | $T_M$ (° C.) | $\Delta H$ (J/G) | IV (DL/G) | APPRX % MOLD FILLED |
|---|---|---|---|---|
| 1 | 223 | 78 | 1.83 | 57 |
| 2 | 228 | 52 | 1.81 | N/A |
| 3 | 224 | 56 | 1.72 | 70 |
| 4 | 221 | 66.5 | 1.58 | N/A |
| 5 | 205 | 43.1 | 1.48 | 73 |
| 6 | 210 | 60 | 1.11 | 83 |
| 7 | 225 | 65 | 0.99 | 100 |

In some embodiments, the fully or partially absorbable barrier, web, mesh or fabric of the present disclosure may further comprise one or more bioactive or therapeutic agents, as well as methods of delivering therapeutic agents. The method comprises the step of applying a mesh or web at a treatment site wherein the mesh or web comprises at least one type of polymeric fiber and one or more bioactive and/or therapeutic agents.

In some embodiments the mesh or web may contain an absorbable polymeric surface coating for controlled drug delivery, wherein one or more bioactive and/or therapeutic agents are dispersed throughout the coating. Alternatively, the mesh or web may contain fibers that are impregnated with one or more bioactive and/or therapeutic agents (see, e.g., U.S. Pat. No. 8,128,954 which is incorporated by reference in its entirety).

In some embodiments, the polymeric surface coating may have multiple coatings or layers of an absorbable aliphatic polyester, and the coating can be applied to the mesh surface. The different coating layers may contain the same or different bioactive and/or therapeutic agents, wherein the agents are present in the same or different concentration in each layer. In some embodiments, the coatings consist of multiple layers, and there is a concentration gradient of bioactive and/or therapeutic agents from the innermost layer to the outermost layer, such that the concentration is highest in the innermost coating layer and lowest in the outermost coating layer. The bioactive agents and/or therapeutic agents may be dispersed within each of the coating layers, or they may be dispersed in only some of the layers, or they may be dispersed in alternating coating layers such that alternating layers lack any bioactive and/or therapeutic agents. Further, the outermost layer may completely lack any bioactive and/or therapeutic agent in order to reduce the potential for a burst release effect. When a gradient concentration design is utilized for dispersing one or more bioactive and/or therapeutic agents throughout the coating layers, it is preferred to have a concentration gradient that decreases from the innermost layer that is closest to the mesh surface to the outermost layer that is the most exterior of all the layers. The concentration gradient is intended to reduce, if not eliminate, an initial burst release of bioactive agents and/or therapeutic agents from the surface of the coating soon after implantation of the mesh.

In some embodiments, the coating polymer is a high molecular weight, caprolactone-based copolymer, wherein caprolactone-derived repeat units make up more than 50% of the repeat units in the total composition, and wherein the remaining repeat units can be derived from monomers selected from L-lactide, glycolide, trimethylene carbonate, and para-dioxanone. When multiple coating layers constitute the surface coating on the mesh or web, each layer may be formed from the same or different caprolactone-based copolymers. Different copolymers will be used when it is desired to modulate the hydrophobic character of different coating layers. Copolymers with higher caprolactone content will be more hydrophobic than copolymers with less caprolactone content. In some embodiments it is desired to have a composition gradient in the different coating layers. For instance, the innermost layer may be formed from a copolymer that is 90% caprolactone, by mole, followed by 80%, 70% and 60% in the adjacent outer layers such that the caprolactone content (and hydrophobic character) decreases from 90% to 60% going from the innermost to the outermost layers. The coating polymers of the present invention are copolymers of caprolactone and trimethylene carbonate.

In a further embodiment, the prepolymer may comprise a semi-crystalline aliphatic polyester copolymer having a heat of fusion <75 J/g, preferably, <70 J/g, more preferably <65 J/g, even more preferably <55 J/g, even more preferably <45 J/g, and even more preferably <35 J/g as measured by DSC. The prepolymer may comprise cyclic monomers such as glycolide, lactide, para-dioxanone, trimethylene carbonate, morpholinedione, and mixtures thereof. The melting point of the prepolymer may be <170° C., more preferably <150° C., even more preferably <120° C., and even more preferably <100° C. as measured by DSC. The resulting prepolymer may be reacted with a flexible linker prior to the crystalline end graft. The flexible linker comprises of a minimum of 10 repeat units, more preferably >20, even more preferably >30 repeat units and even more preferably >40. The flexible linker may comprise an amorphous segment with a composition including cyclic monomers such as glycolide, lactide, para-dioxanone, ε-caprolactone, trimethylene carbonate, morpholinedione, and mixtures thereof. The crystalline end graft may be a high lactide copolymer that contains minor amounts of at least one additional monomer. By "high" it is meant that polymers may contain at least 50% by mole of lactide-derived repeat units, at least 55%, 60%, 65%, 70%, 75%, 80%, 85%, 90%, 95%, or higher of lactide-derived repeat units. Ranges of lactide molar content are also envisioned as within the scope of this disclosure including ranges of 50-60%, 60-70%, 70-80%, 80-90%, and 90-100%. In addition, the crystalline end graft may contain at least 50% by mole of glycolide-derived repeat units, at least 55%, 60%, 65%, 70%, 75%, 80%, 85%, 90%, 95%, or higher of glycolide-derived repeat units. (See FIG. 12.) Ranges of glycolide molar content are also envisioned as within the scope of this disclosure including ranges of 50-60%, 60-70%, 70-80%, 80-90%, and 90-100%. (See FIG. 12.) The overall polymer may comprise initiators that are linear or polyaxial.

In a further embodiment, a second polymer may be combined or blended with an improved block copolymer of the present disclosure. The second polymer may be a reinforcing additive that provides higher strength to compositions comprising the block copolymers. This is particularly suitable when the amount of prepolymer present within the block copolymer is greater than 25% by weight of the overall polymer, and even more so in cases where the prepolymer is approaching 50%. The additional polymer allows for a block copolymer unable to crystallize to an extent necessary to provide desired mechanical strength, to actually crystallize in the presence of the additive. This results in a higher degree of crystallinity or percent crystallinity for the blended composition. Further, the reinforcing polymer may have a chain length approximately double the chain length of a single terminal block of the block copolymer. The additional, reinforcing polymers may not have shorter chain lengths as they will not reinforce the block copolymer by forming the physical entanglements between two or more terminal end blocks of block copolymers disclosed herein, which may be linear or polyaxial. The reinforcing polymer may have the same theoretical chemical composition and therefore may be derived from the same monomers as the repeat units forming the terminal blocks of the block copolymer. Polymerization of the terminal blocks may include residual monomer from the reaction forming either the prepolymer or flexible linking segment.

Applying a surface coating to a mesh construct can be accomplished by dip coating or spray coating techniques using a liquid solution of polymer mixed with one or more therapeutic agents at a specific concentration. Alternatively, the liquid solution may contain polymer without any therapeutic agent. Mixing and dissolution can be accomplished by combining the caprolactone-based coating polymers with a common organic solvent and a specific amount of therapeutic agent. This yields a solution with a specific concentration of therapeutic agent that can be applied to the mesh surface by dip coating or spray coating. To create multiple coating layers, different solutions can be applied to the mesh surface sequentially. Each solution can contain different concentrations of one or more therapeutic agents so that a concentration gradient can be created throughout the surface coating, and/or each solution can contain polymers of different hydrophobic character.

In an alternative embodiment, biocompatible polymeric compositions containing a therapeutic agent can be prepared by the cold-worked or hot-worked method, depending on the heat-resistance of the therapeutic agent. For therapeutic agents that are likely to be inactivated by heat, the cold-worked method is preferred. Briefly, the polymer components of the mesh or web, either the major component, the minor component or both, may be completely melted in the absence of the therapeutic agent. The melted composition is cooled to room temperature or below to delay crystallization of the polymer in the composition. In certain embodiments, the cooling is conducted at a rate of about 10° C. per minute. The therapeutic agent is then added to the melted composition at room temperature or below and mixed thoroughly with the composition to create a homogeneous blend. Solution-based mixing procedures may also be employed depending on the nature of the materials.

In an alternative embodiment, the barrier, mesh or web of the current disclosure may have the bioactive and/or therapeutic agents applied to one or more specific sections of the mesh or web, as opposed to the entire construct. Within certain embodiments, the mesh or web can be either dip-coated or spray-coated with one or more bioactive agents, or with a composition which releases one or more bioactive agents over a desired time frame. In yet other embodiments, the fibers themselves may be constructed to release the bioactive agent(s) (see e.g., U.S. Pat. No. 8,128,954 which is incorporated by reference in its entirety).

The therapeutic agents may include fibrosis-inducing agents, antifungal agents, antibacterial agents, anti-inflammatory agents, anti-adhesion agents, osteogenesis and calcification promoting agents, antibacterial agents and antibiotics, immunosuppressive agents, immunostimulatory agents, antiseptics, anesthetics, antioxidants, cell/tissue growth promoting factors, lipopolysaccharide complexing agents, peroxides, anti-scarring agents, anti-neoplastic, anti-cancer agents and agents that support ECM integration.

Examples of fibrosis-inducing agents include, but are not limited to talcum powder, metallic beryllium and oxides thereof, copper, silk, silica, crystalline silicates, talc, quartz dust, and ethanol; a component of extracellular matrix selected from fibronectin, collagen, fibrin, or fibrinogen; a polymer selected from the group consisting of polylysine, poly(ethylene-co-vinylacetate), chitosan, N-carboxybutylchitosan, and RGD proteins; vinyl chloride or a polymer of vinyl chloride; an adhesive selected from the group consisting of cyanoacrylates and crosslinked poly(ethylene glycol)-methylated collagen; an inflammatory cytokine (e.g., TGF-.beta., PDGF, VEGF, bFGF, TNF.alpha., NGF, GM-CSF, IGF-a, IL-1, IL-1-.beta., IL-8, IL-6, and growth hormone); connective tissue growth factor (CTGF); a bone morphogenic protein (BMP) (e.g., BMP-2, BMP-3, BMP-4, BMP-5, BMP-6, or BMP-7); leptin, and bleomycin or an analogue or derivative thereof. Optionally, the device may additionally comprise a proliferative agent that stimulates cellular proliferation. Examples of proliferative agents include: dexamethasone, isotretinoin (13-cis retinoic acid), 17-e-estradiol, estradiol, 1-a-25 dihydroxyvitamin $D_3$, diethylstibesterol, cyclosporine A, L-NAME, all-trans retinoic acid (ATRA), and analogues and derivatives thereof. (see US Pat. Pub. No. 2006/0240063, which is incorporated by reference in its entirety).

Examples of antifungal agents include, but are not limited to polyene antifungals, azole antifungal drugs, and Echinocandins.

Examples of antibacterial agents and antibiotics include, but are not limited to erythromycin, penicillins, cephalosporins, doxycycline, gentamicin, vancomycin, tobramycin, clindamycin, and mitomycin.

Examples of anti-inflammatory agents include, but are not limited to non-steroidal anti-inflammatory drugs such as ketorolac, naproxen, diclofenac sodium and flurbiprofen.

Examples of anti-adhesion agents include, but are not limited to talcum powder, metallic beryllium and oxides thereof, copper, silk, silica, crystalline silicates, talc, quartz dust, and ethanol.

Examples of osteogenesis or calcification promoting agents include, but are not limited to bone fillers such as hydroxyapatite, tricalcium phosphate, calcium chloride, calcium carbonate, calcium sulfate, bioactive glasses, bone morphogenic proteins (BMPs), such as BMP-2, BMP-3, BMP-4, BMP-5, BMP-6, and BMP-7.

Examples of immunosuppressive agents include, but are not limited to glucocorticoids, alkylating agents, antimetabolites, and drugs acting on immunophilins such as ciclosporin and tacrolimus.

Examples of immunostimulatory agents include, but are not limited to interleukins, interferon, cytokines, toll-like receptor (TLR) agonists, cytokine receptor agonist, CD40 agonist, Fc receptor agonist, CpG-containing immunostimulatory nucleic acid, complement receptor agonist, or an adjuvant.

Examples of antiseptics include, but are not limited to chlorhexidine and tibezonium iodide.

Examples of antioxidants include, but are not limited to antioxidant vitamins, carotenoids, and flavonoids.

Examples of anesthetic include, but are not limited to lidocaine, mepivacaine, pyrrocaine, bupivacaine, prilocalne, and etidocaine.

Examples of cell growth promoting factors include but are not limited to, epidermal growth factors, human platelet derived tgf-b, endothelial cell growth factors, thymocyte-activating factors, platelet derived growth factors, fibroblast growth factor, fibronectin or laminin.

Examples of lipopolysaccharide complexing agents include, but are not limited to polymyxin.

Examples of peroxides, include, but are not limited to benzoyl peroxide and hydrogen peroxide.

Examples of antineoplastic/anti-cancer agents include, but are not limited to paclitaxel, carboplatin, miconazole, leflunamide, and ciprofloxacin.

Examples of anti-scarring agents include, but are not limited to cell-cycle inhibitors such as a taxane, immunomodulatory agents such as serolimus or biolimus (see, e.g., paras. 64 to 363, as well as all of us U.S. Pat. Pub. No. 2005/0149158, which is incorporated herein by reference in its entirety).

Examples of agents that support ECM integration include, but are not limited to gentamicin.

It is recognized that in certain forms of therapy, combinations of agents/drugs in the same polymeric composition can be useful in order to obtain an optimal effect. Thus, for example, an antibacterial and an anti-inflammatory agent may be combined in a single copolymer to provide combined effectiveness.

The disclosure herein may be used in association with injection molded articles, films, nonporous films, drug delivery vehicles, particulate micro/nano drug delivery vehicles, meshes, nonwoven articles, knitted, woven, surgical meshes, bioabsorbable stents for body lumens, 3-D printed articles, drug coatings, transient implants and components thereof, and in situ forming medical articles.

Unless specifically stated, terms and phrases used in this document, and variations thereof, unless otherwise expressly stated, should be construed as open ended as opposed to limiting. Likewise, a group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise.

Furthermore, although items, elements or components of the disclosure may be described or claimed in the singular, the plural is contemplated to be within the scope thereof unless limitation to the singular is explicitly stated. The presence of broadening words and phrases such as "one or more," "at least," "but not limited to" or other like phrases in some instances shall not be read to mean that the narrower case is intended or required in instances where such broadening phrases may be absent.

While the present subject matter has been described in detail with respect to specific exemplary embodiments and methods thereof, it will be appreciated that those skilled in the art, upon attaining an understanding of the foregoing may readily produce alterations to, variations of, and equivalents to such embodiments. Accordingly, the scope of the present disclosure is byway of example rather than by way of limitation, and the subject disclosure does not preclude inclusion of such modifications, variations and/or additions to the present subject matter as would be readily apparent to one of ordinary skill in the art using the teachings disclosed herein.

What is claimed is:

1. A method for producing an absorbable glycolide based, aliphatic polyester copolymer comprising trimethylene carbonate (TMC) prepolymer having multiple axes and crystalline end grafts emanating from each of said axes, and having a melting temperature, said method comprising:

end-grafting by ring-opening polymerization said trimethylene carbonate (TMC) prepolymer in the presence of a ring-opening polymerization catalyst with cyclic monomers glycolide and ε-caprolactone, wherein the end graft comprises more than 90% glycolide;

wherein a molar ratio of the total amount of said monomers to the total amount of said ring opening polymerization catalyst is higher than 90,000, and wherein during melt processing of the absorbable aliphatic polyester copolymer, the absorbable aliphatic polyester copolymer has an increased thermal degradation onset temperature compared to the thermal degradation onset temperature of an absorbable aliphatic polyester copolymer made with a lower monomer:catalyst ratio.

2. The method of claim 1, wherein the ring opening polymerization catalyst is stannous octanoate.

3. The method of claim 1 wherein the trimethylene carbonate (TMC) prepolymer is heated to a temperature of greater than 110° C.

4. The method of claim 1 wherein the trimethylene carbonate (TMC) prepolymer is heated to a temperature of greater than 130° C.

5. The method of claim 1, wherein the trimethylene carbonate (TMC) prepolymer has a molecular weight of greater than 10 kDa.

6. The method of claim 1, wherein the trimethylene carbonate (TMC) prepolymer has a molecular weight of greater than 20 kDa.

7. A method for producing an absorbable glycolide based, aliphatic polyester copolymer having increased thermal degradation onset temperature with an amorphous prepolymer forming multiple axes and crystalline end grafts emanating from each of said axes, said method comprising:
  a) preparing an amorphous prepolymer comprising a first cyclic monomer comprising trimethylene carbonate (TMC), in the presence of an initiator having plural alcohol groups and in the presence of a ring opening polymerization catalyst; and;
  b) end-grafting by ring-opening polymerization the trimethylene carbonate (TMC) prepolymer of a) with second cyclic monomers of glycolide and ε-caprolactone, wherein the end graft comprises more than 90% glycolide, in the presence of a ring opening polymerization catalyst;
  wherein a molar ratio of the total amount of said first and second cyclic monomers to the total amount of said ring opening polymerization catalyst is higher than 90,000, wherein during melt processing of the absorbable aliphatic polyester copolymer, the absorbable aliphatic polyester copolymer has an increased thermal degradation onset temperature compared to the thermal degradation onset temperature of an absorbable aliphatic polyester copolymer made with a lower monomer:catalyst ratio.

8. The method of claim 7, wherein the trimethylene carbonate (TMC) prepolymer is heated to a temperature of greater than 130° C. in b).

9. The method of claim 7, wherein the trimethylene carbonate (TMC) prepolymer has a molecular weight of greater than 10 kDa.

10. The method of claim 7, wherein the trimethylene carbonate (TMC) prepolymer has a molecular weight of greater than 20 kDa.

11. The method of claim 7, wherein the ring opening polymerization catalyst is stannous octanoate.

* * * * *